US012702500B2

(12) United States Patent
Ogimoto et al.

(10) Patent No.: US 12,702,500 B2
(45) Date of Patent: Aug. 11, 2026

(54) CONTROLLER, ENDOSCOPE SYSTEM, AND CONTROL METHOD

(71) Applicants: OLYMPUS CORPORATION, Tokyo (JP); National Cancer Center, Tokyo (JP)

(72) Inventors: Hiroto Ogimoto, Tokyo (JP); Ryota Sasai, Tokyo (JP); Masaru Yanagihara, Tokyo (JP); Hiro Hasegawa, Tokyo (JP); Daichi Kitaguchi, Tokyo (JP); Nobuyoshi Takeshita, Tokyo (JP); Shigehiro Kojima, Tokyo (JP); Yuki Furusawa, Tokyo (JP); Yumi Kinebuchi, Tokyo (JP); Masaaki Ito, Tokyo (JP)

(73) Assignees: OLYMPUS CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 523 days.

(21) Appl. No.: 18/105,305

(22) Filed: Feb. 3, 2023

(65) Prior Publication Data

US 2023/0172675 A1 Jun. 8, 2023

Related U.S. Application Data

(63) Continuation of application No. PCT/JP2021/033205, filed on Sep. 9, 2021.

(Continued)

(51) Int. Cl.

*A61B 34/30* (2016.01)
*A61B 1/00* (2006.01)

(Continued)

(52) U.S. Cl.

CPC .......... *A61B 34/30* (2016.02); *A61B 1/00006* (2013.01); *A61B 1/00009* (2013.01);

(Continued)

(58) Field of Classification Search

CPC ............ A61B 1/00006; A61B 1/00149; A61B 1/3132; A61B 90/361; A61B 90/50; A61B 2034/2065; A61B 34/30

See application file for complete search history.

(56) References Cited

U.S. PATENT DOCUMENTS

| | | | |
|---|---|---|---|
| 5,416,513 | A | 5/1995 | Morisaki |
| 6,471,637 | B1 | 10/2002 | Green et al. |

(Continued)

FOREIGN PATENT DOCUMENTS

| | | | |
|---|---|---|---|
| EP | 1820438 | A1 | 8/2007 |
| EP | 1854420 | A1 | 11/2007 |

(Continued)

OTHER PUBLICATIONS

US Office Action issued Aug. 22, 2024 in U.S. Appl. No. 18/105,291.

(Continued)

*Primary Examiner* — Alexandra L Newton

(74) *Attorney, Agent, or Firm* — Scully, Scott, Murphy & Presser, P.C.

(57) ABSTRACT

A controller controls a movement of an endoscope to cause the endoscope to follow a surgical instrument. The controller includes a processor. The processor acquires position information including the position of the surgical instrument, acquires scene information associated with a procedure scene to be observed through the endoscope, determines an offset parameter, which determines the position of the target point with respect to a predetermined fiducial point in the field of view of the endoscope, of a target point on the basis of the scene information, sets the position of the target point (Continued)

with respect to the fiducial point on the basis of the offset parameter, and causes the endoscope to follow the surgical instrument such that the surgical instrument is disposed at the target point, by controlling a movement of the endoscope on the basis of the position of the target point and the position of the surgical instrument.

14 Claims, 23 Drawing Sheets

Related U.S. Application Data

(60) Provisional application No. 63/076,408, filed on Sep. 10, 2020.

(51) Int. Cl.

| | |
|---|---|
| ***A61B 1/045*** | (2006.01) |
| ***A61B 5/06*** | (2006.01) |
| ***A61B 34/20*** | (2016.01) |
| ***G06T 3/60*** | (2024.01) |
| ***G06T 7/70*** | (2017.01) |
| ***H04N 23/62*** | (2023.01) |
| ***H04N 23/667*** | (2023.01) |

(52) U.S. Cl.

CPC ........ *A61B 1/0004* (2022.02); *A61B 1/00042* (2022.02); *A61B 1/00045* (2013.01); *A61B 1/00149* (2013.01); *A61B 1/045* (2013.01); *A61B 5/065* (2013.01); *G06T 3/60* (2013.01); *G06T 7/70* (2017.01); *H04N 23/62* (2023.01); *H04N 23/667* (2023.01); *A61B 2034/2055* (2016.02); *A61B 2034/2065* (2016.02); *A61B 2034/301* (2016.02); *A61B 2034/305* (2016.02); *G06T 2207/10012* (2013.01); *G06T 2207/10068* (2013.01); *G06T 2207/30004* (2013.01); *G06T 2207/30244* (2013.01)

(56) References Cited

U.S. PATENT DOCUMENTS

| | | | | |
|---|---|---|---|---|
| 9,937,013 | B2 | 4/2018 | Frimer et al. | |
| 10,729,502 | B1 | 8/2020 | Wolf et al. | |
| 2002/0156345 | A1 | 10/2002 | Eppler et al. | |
| 2002/0161280 | A1 | 10/2002 | Chatenever et al. | |
| 2003/0055437 | A1 | 3/2003 | Yasunaga | |
| 2005/0020883 | A1 | 1/2005 | Chatenever et al. | |
| 2005/0027167 | A1 | 2/2005 | Chatenever et al. | |
| 2005/0123179 | A1 | 6/2005 | Chen et al. | |
| 2007/0232863 | A1 | 10/2007 | Miyake et al. | |
| 2007/0265502 | A1 | 11/2007 | Minosawa et al. | |
| 2013/0331644 | A1 | 12/2013 | Pandya et al. | |
| 2014/0005475 | A1 | 1/2014 | Song et al. | |
| 2014/0194896 | A1 | 7/2014 | Frimer et al. | |
| 2016/0007827 | A1 | 1/2016 | Frimer et al. | |
| 2016/0007828 | A1 | 1/2016 | Frimer et al. | |
| 2016/0007836 | A1 | 1/2016 | Kikuchi | |
| 2016/0051336 | A1 | 2/2016 | Frimer et al. | |
| 2016/0174955 | A1 | 6/2016 | Frimer et al. | |
| 2016/0270864 | A1 | 9/2016 | Frimer et al. | |
| 2016/0353970 | A1 | 12/2016 | Inoue | |
| 2017/0027654 | A1 | 2/2017 | Frimer et al. | |
| 2018/0140168 | A1 | 5/2018 | Haraguchi | |
| 2019/0000585 | A1 | 1/2019 | Kokubo et al. | |
| 2019/0090728 | A1 | 3/2019 | Fanenbruck et al. | |
| 2019/0117323 | A1 | 4/2019 | Frimer et al. | |
| 2019/0183321 | A1 | 6/2019 | Teranuma | |
| 2019/0209124 | A1 | 7/2019 | Taniguchi | |
| 2019/0365499 | A1 | 12/2019 | Nagao et al. | |
| 2020/0015655 | A1 | 1/2020 | Taguchi | |
| 2020/0113419 | A1* | 4/2020 | Inoue | G06T 7/30 |
| 2020/0297200 | A1 | 9/2020 | Okada | |
| 2020/0297422 | A1 | 9/2020 | Gocho et al. | |
| 2020/0383736 | A1 | 12/2020 | Frimer et al. | |
| 2021/0212790 | A1 | 7/2021 | Yoshimura et al. | |
| 2022/0079415 | A1 | 3/2022 | Christian et al. | |
| 2022/0192777 | A1* | 6/2022 | Kuroda | A61B 34/10 |
| 2022/0354347 | A1 | 11/2022 | Nishimura et al. | |
| 2022/0408002 | A1 | 12/2022 | Birkenbach | |

FOREIGN PATENT DOCUMENTS

| | | | | |
|---|---|---|---|---|
| EP | 2979610 | A1 | 2/2016 | |
| JP | H05284411 | A | 10/1993 | |
| JP | H05337118 | A | 12/1993 | |
| JP | H06319697 | A | 11/1994 | |
| JP | H0723271 | A | 1/1995 | |
| JP | H07194610 | A | 8/1995 | |
| JP | H0938030 | A | 2/1997 | |
| JP | H09266882 | A | 10/1997 | |
| JP | 2001112704 | A | 4/2001 | |
| JP | 2003088532 | A | 3/2003 | |
| JP | 2003127076 | A | 5/2003 | |
| JP | 2005055756 | A | 3/2005 | |
| JP | 2006229322 | A | 8/2006 | |
| JP | 2007222239 | A | 9/2007 | |
| JP | 2007301378 | A | 11/2007 | |
| JP | 2013192803 | A | 9/2013 | |
| JP | 6161687 | B2 | 7/2017 | |
| JP | 2019162231 | A | 9/2019 | |
| WO | 2005062253 | A1 | 7/2005 | |
| WO | 2018051565 | A1 | 3/2018 | |
| WO | 2018179681 | A1 | 10/2018 | |
| WO | WO-2018235255 | A1 * | 12/2018 | G06T 7/246 |
| WO | 2019116592 | A1 | 6/2019 | |
| WO | 2019181149 | A1 | 9/2019 | |
| WO | 2020070883 | A1 | 4/2020 | |

OTHER PUBLICATIONS

Bihlmaier, A., "Learning Dynamic Spatial Relations, The Case of a Knowledge-based Endoscopic Camera Guidance Robot", pp. 23-102, Springer Link, https://link.springer.com/book/10.1007/978-3-658-14914-7 (2016).
International Search Report dated Sep. 28, 2021 issued in PCT/JP2021/027564.
International Search Report dated Nov. 22, 2021 issued in PCT/JP2021/033205.
International Search Report dated Nov. 22, 2021 issued in PCT/JP2021/033209.
International Search Report dated Nov. 16, 2021 issued in PCT/JP2021/033210.
Related U.S. Appl. No. 18/105,291, filed Feb. 3, 2023.
Related U.S. Appl. No. 18/105,300, filed Feb. 3, 2023.
Related U.S. Appl. No. 18/105,314, filed Feb. 3, 2023.
US Office Action dated Sep. 10, 2025 received in U.S. Appl. No. 18/105,300.
US Office Action dated Sep. 24, 2025 received in U.S. Appl. No. 18/105,314.

* cited by examiner

CONTROLLER, ENDOSCOPE SYSTEM, AND CONTROL METHOD

TECHNICAL FIELD

The present invention relates to a controller, an endoscope system, and a control method and particularly relates to a controller, an endoscope system, and a control method, by which an endoscope is controlled to follow a surgical instrument.

The present application claims priority under the provisional U.S. patent application No. 63/076,408 filed on Sep. 10, 2020, which is incorporated herein by reference. This is a continuation of International Application PCT/JP2021/033205 which is hereby incorporated by reference herein in its entirety.

BACKGROUND ART

In laparoscopic surgery, a surgeon operates a surgical instrument while observing the surgical instrument in an endoscope image displayed on the screen of a monitor. If the surgical instrument is placed on an edge of the endoscope image or moved out of the endoscope image, the surgeon may feel greater stress or the surgery may become hard to continue. Thus, it is important to keep the position of the surgical instrument around the center of the endoscope image. In this connection, a device is proposed to keep the position of a surgical instrument around the center of an endoscope image by causing an endoscope to follow the surgical instrument (for example, see PTL 1).

CITATION LIST

Patent Literature

{PTL 1} Japanese Unexamined Patent Application Publication No. Hei 5-337118

SUMMARY OF INVENTION

An aspect of the present invention is a controller that controls a movement of an endoscope to cause the endoscope to follow a surgical instrument, the controller including a processor, wherein the processor acquires position information including the position of the surgical instrument, the processor acquires scene information that is information associated with a procedure scene to be observed through the endoscope, the processor determines an offset parameter of a target point on the basis of the scene information, the offset parameter being a parameter that determines the position of the target point with respect to a predetermined fiducial point in the field of view of the endoscope, the processor sets the position of the target point with respect to the fiducial point on the basis of the offset parameter, and the processor causes the endoscope to follow the surgical instrument such that the surgical instrument is disposed at the target point, by controlling a movement of the endoscope on the basis of the position of the target point and the position of the surgical instrument.

Another aspect of the present invention is a controller that controls a movement of an endoscope to cause the endoscope to follow a surgical instrument, the controller including a processor, wherein the processor acquires position information from an image of a subject, the processor estimates a procedure scene from the image, and the processor determines a position of the surgical instrument in a field of view of the endoscope on a basis of the procedure scene.

Another aspect of the present invention is an endoscope system including an endoscope, a moving device that moves the endoscope in a subject, and the controller that controls the moving device to cause the endoscope to follow a surgical instrument.

Another aspect of the present invention is a control method that controls a movement of an endoscope to cause the endoscope to follow a surgical instrument, the control method including: acquiring position information including the position of the surgical instrument; acquiring scene information that is information associated with a procedure scene to be observed through the endoscope; determining an offset parameter of a target point on the basis of the scene information, the offset parameter being a parameter that determines the position of the target point with respect to a predetermined fiducial point in the field of view of the endoscope; setting the position of the target point with respect to the fiducial point on the basis of the offset parameter, and causing the endoscope to follow the surgical instrument such that the surgical instrument is disposed at the target point, by controlling a movement of the endoscope on the basis of the position of the target point and the position of the surgical instrument.

DESCRIPTION OF EMBODIMENTS

First Embodiment

A controller, an endoscope system, and a control method according to a first embodiment of the present invention will be described below with reference to the accompanying drawings.

Figure 1:
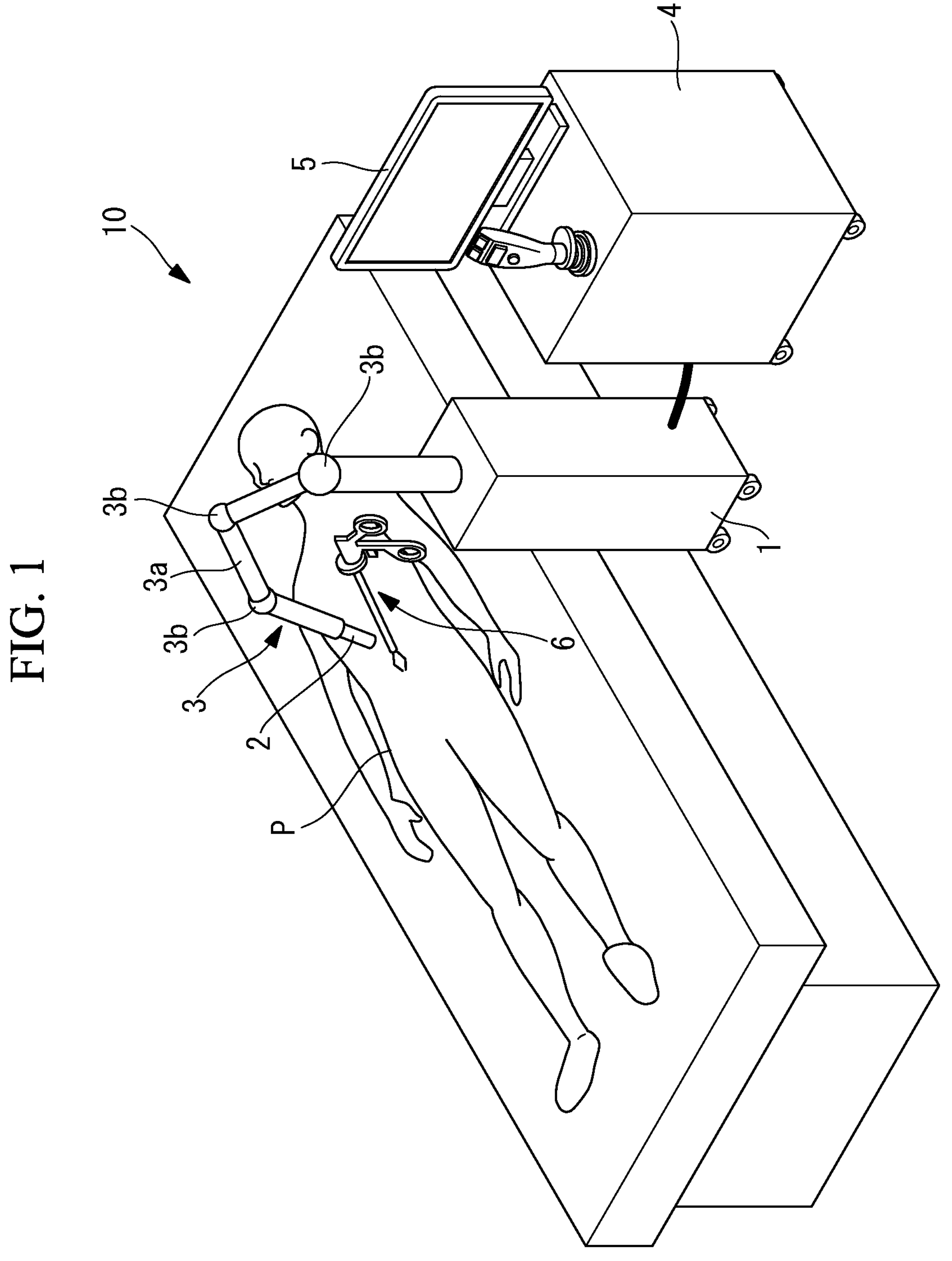
FIG. 1 illustrates an appearance of the overall configuration of an endoscope system according to a first embodiment.

As illustrated in FIG. 1, an endoscope system 10 according to the present embodiment is used for a surgical operation in which an endoscope 2 and at least one surgical instrument 6 are inserted into the body of a patient P serving as a subject and an affected part is treated with the surgical instrument 6 while the surgical instrument 6 is observed through the endoscope 2. The endoscope system 10 is used for, for example, laparoscopic surgery.

Figure 2A:
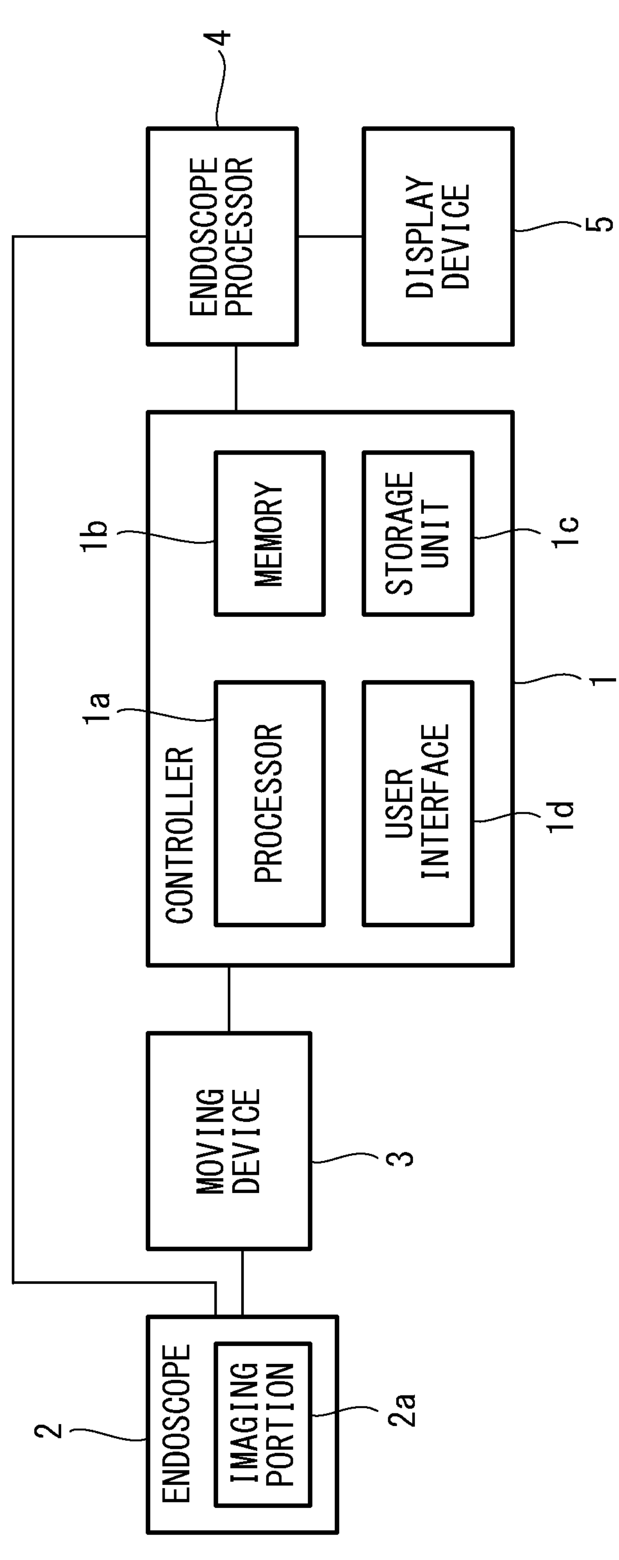
FIG. 2A is a block diagram illustrating the overall configuration of the endoscope system in FIG. 1.

As illustrated in FIGS. 1 and 2A, the endoscope system 10 includes the endoscope 2, a moving device 3 that moves the endoscope 2 in the body of the patient P, an endoscope processor 4 that is connected to the endoscope 2 and processes an endoscope image captured by the endoscope 2, a controller 1 that is connected to the moving device 3 and the endoscope processor 4 and controls the moving device 3, and a display device 5 that is connected to the endoscope processor 4 and displays the endoscope image.

The endoscope 2 is, for example, a rigid endoscope and includes an imaging portion 2*a* that has an image sensor and captures an endoscope image B. The imaging portion 2*a* is, for example, a three-dimensional camera provided at the tip portion of the endoscope 2 and captures a stereo image, which includes a tip 6*a* of the surgical instrument 6, as the endoscope image B (for example, see FIG. 3B). For example, the imaging portion 2*a* is an image sensor such as a CCD (Charge Coupled Device) image sensor or a CMOS (Complementary Metal Oxide Semiconductor) image sensor. The imaging portion 2*a* generates an image of a predetermined region by converting received light from the predetermined region into an electric signal through photoelectric conversion. A stereo image as the endoscope image B is generated by performing image processing on two images with a parallax through the endoscope processor 4 or the like.

The endoscope image B is transmitted from the endoscope 2 to the endoscope processor 4, is subjected to necessary processing in the endoscope processor 4, is transmitted from the endoscope processor 4 to the display device 5, and is displayed on the display device 5. A surgeon operates the surgical instrument 6 in a body while observing the endoscope image B displayed on the display device 5. The display device 5 may be any display, for example, a liquid crystal display or an organic electroluminescent display. The display device 5 may include an audio system, for example, a speaker.

In addition to the display device 5, a user terminal for communications with the controller 1 and the endoscope processor 4 via a communication network may be provided to display the endoscope image B at the terminal. The terminal is, for example, a notebook computer, a laptop computer, a tablet computer, or a smartphone but is not particularly limited thereto.

The moving device 3 includes a robot arm 3*a* (including an electric scope holder) that is connected to the proximal end of the endoscope 2 and three-dimensionally controls the position and orientation of the endoscope 2. The moving device 3 in FIG. 1 includes the robot arm 3*a* having a plurality of joints 3*b* that operate to three-dimensionally move the endoscope 2, thereby three-dimensionally changing the position and orientation of the endoscope 2.

As illustrated in FIG. 2A, the controller 1 includes at least one processor 1*a* like a central processing unit, a memory 1*b*, a storage unit 1*c*, and a user interface 1*d*. The controller 1 may be, for example, a desktop computer, a tablet computer, a laptop computer, a smartphone, or a cellular phone.

The processor 1*a* may be a single processor, a multiprocessor, or a multicore processor. The processor 1*a* reads and executes a program stored in the storage unit 1*c*.

The memory 1*b* is, for example, a semiconductor memory including a ROM (read-only memory) or RAM (Random Access Memory) area. The memory 1*b* may store data necessary for the processing of the processor 1*a* (that is, the memory 1*b* may operate as a "storage unit") like the storage unit 1*c*, which will be described later.

The storage unit 1*c* is a hard disk or a nonvolatile recording medium including a semiconductor memory such as flash memory and stores a program and data necessary for causing the processor 1*a* to perform processing. The processor 1*a* performs processing according to the program read in the memory 1*b*, thereby implementing the functions of units 11, 12, 13, and 14, which will be described later. Some of the functions of the controller 1 may be implemented by dedicated logic circuits or hardware, for example, an FPGA (Field Programmable Gate Array), a SoC (System-on-a-Chip), an ASIC (Application Specific Integrated Circuit), and a PLD (Programmable Logic Device).

The controller 1 has a manual mode and a follow-up mode and switches the manual mode and the follow-up mode on the basis of an instruction of an operator, e.g., a surgeon, for example, on the basis of an operator's voice.

The manual mode is a mode that permits an operator to manually operate the endoscope 2. In the manual mode, for example, the operator can remotely operate the robot arm 3*a* or an electric holder by operating an operating device (not illustrated) connected to the controller 1.

The follow-up mode is a mode in which the moving device 3 is controlled by the controller 1 to cause the endoscope 2 to automatically follow the surgical instrument 6 set to be followed.

Figure 3A:
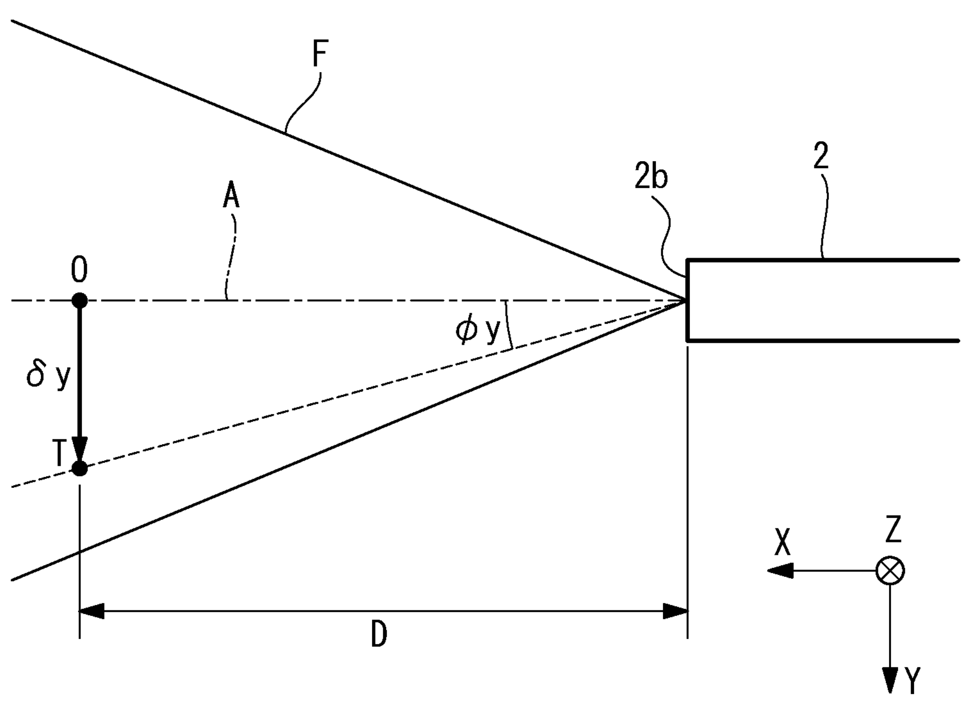
FIG. 3A is an explanatory drawing of a fiducial point and a target point that are set in the field of view of an endoscope.
Figure 3B:
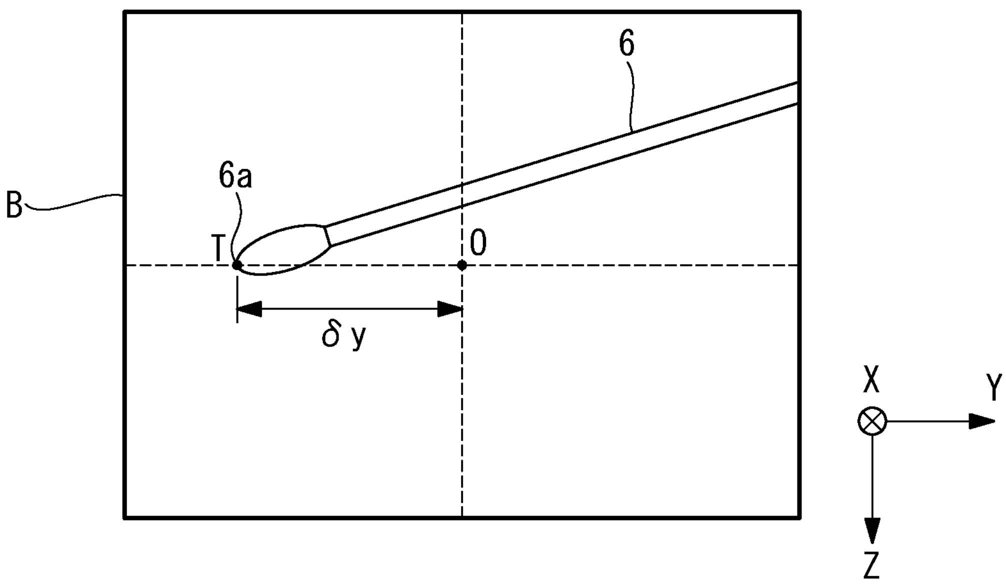
FIG. 3B is an explanatory drawing of the fiducial point and the target point in an endoscope image.

As illustrated in FIGS. 3A and 3B, in the follow-up mode, the controller 1 acquires the three-dimensional position of the tip 6*a* of the surgical instrument 6 and controls the moving device 3 on the basis of the three-dimensional position of the tip 6*a* and the three-dimensional position of a target point T in a field of view F. Thus, the controller 1 controls a movement of the endoscope 2 and causes the endoscope 2 to follow the surgical instrument 6 such that the target point T is disposed at the tip 6*a*.

In FIGS. 3A and 3B, a direction parallel to an optical axis A of the endoscope 2 is X direction, a direction that is orthogonal to the optical axis A and corresponds to the lateral direction of the endoscope image B is Y direction, and a direction that is orthogonal to the optical axis A and corresponds to the longitudinal direction of the endoscope image B is Z direction.

The target point T is initially set at a fiducial point O on the optical axis A, the fiducial point O being disposed at a predetermined distance D from a tip 2*b* of the endoscope 2 in a direction parallel to the optical axis A. The controller 1 causes the target point T to three-dimensionally have an offset from the fiducial point O to another position in the field of view F according to a procedure scene observed by the endoscope 2. Thus, the position of the tip 6*a* in the endoscope image B changes between the center of the endoscope image B and an offset position from the center according to a procedure scene.

Figure 2B:
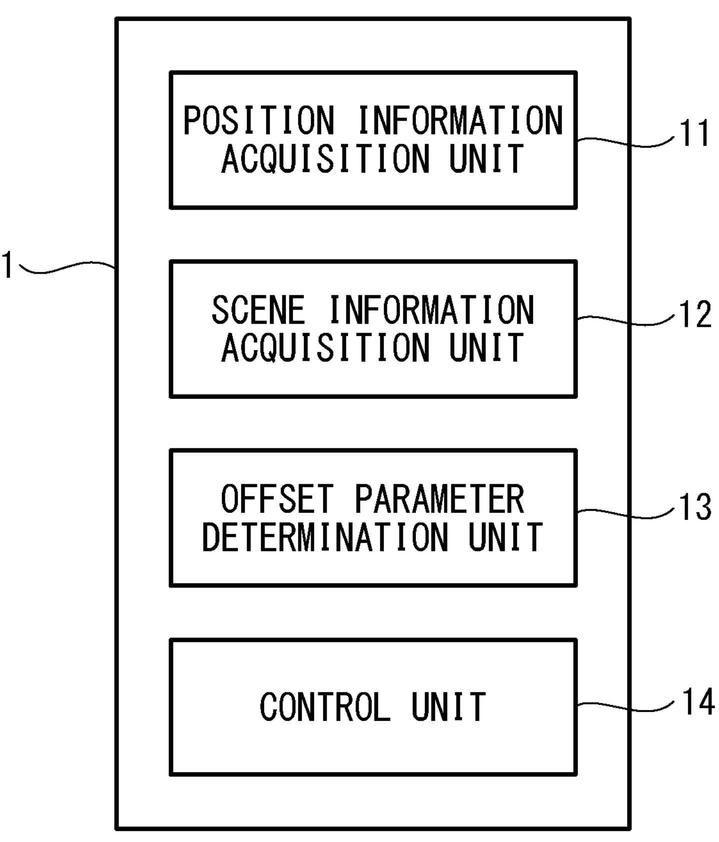
FIG. 2B is a functional block diagram illustrating a controller for the endoscope system in FIG. 1.

Specifically, as illustrated in FIG. 2B, the controller 1 includes the position information acquisition unit 11 that acquires position information, the scene information acquisition unit 12 that acquires scene information, the offset parameter determination unit 13 that determines an offset parameter on the basis of the scene information, and the control unit 14 that controls the position and orientation of the endoscope 2 on the basis of the offset parameter and the position information.

The position information acquisition unit 11 acquires position information on an object present in the endoscope image B, from the endoscope processor 4. The position information includes at least the three-dimensional position of the tip 6*a* of the surgical instrument 6. Thus, the endoscope processor 4 performs processing for calculating position information including the three-dimensional position of the tip 6*a* from the endoscope image B. The processing for calculating position information may be performed by the position information acquisition unit 11.

The scene information is information associated with a procedure scene to be observed through the endoscope 2. A motion of the surgical instrument 6 varies according to a procedure scene. For example, in a scene of the ablating of a biological tissue by the surgical instrument 6, a surgeon slowly moves the surgical instrument 6. The scene information acquisition unit 12 acquires a three-dimensional moving vector (velocity vector) V of the surgical instrument 6 as scene information, the moving vector indicating a motion of the surgical instrument 6.

Figure 4A:
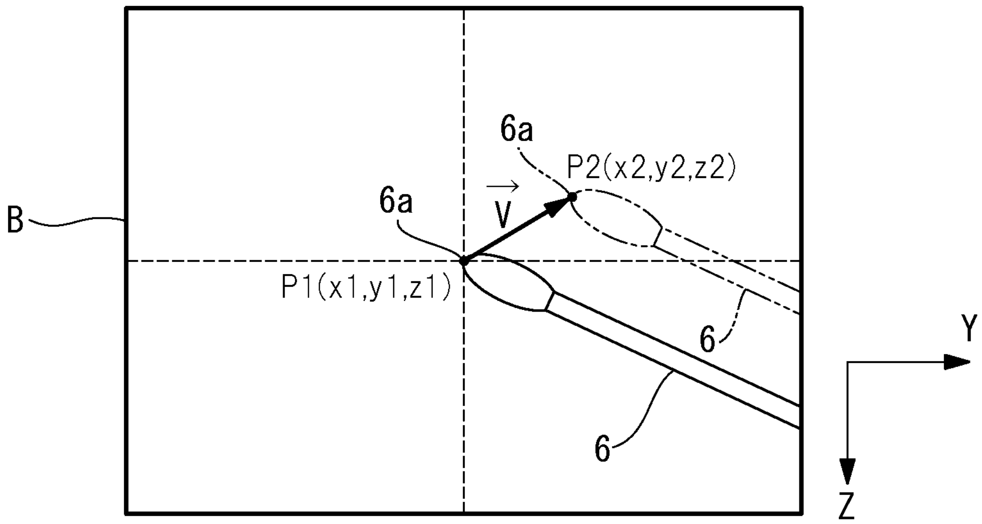
FIG. 4A is an explanatory drawing of an example of a method for detecting the moving vector of a surgical instrument.
Figure 5:
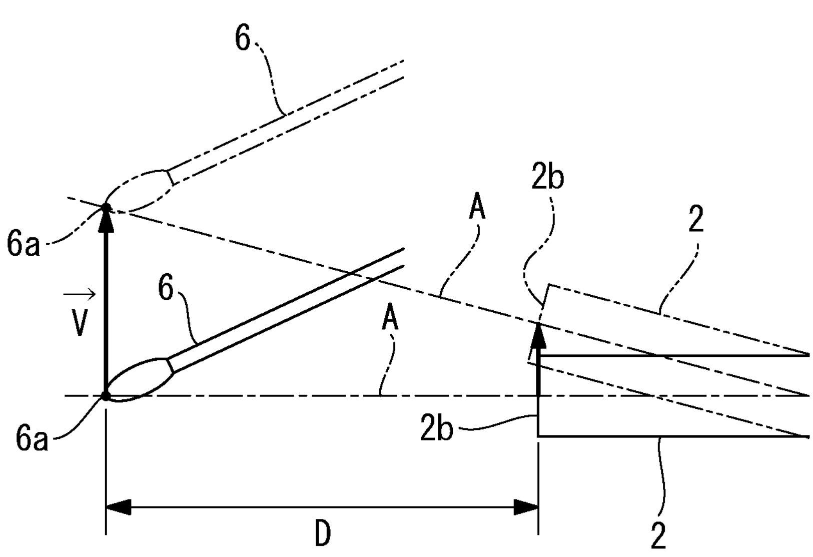
FIG. 5 is an explanatory drawing of another example of the method for detecting the moving vector of the surgical instrument.

For example, the scene information acquisition unit 12 detects the moving vector V from the endoscope image B as illustrated in FIG. 4A or detects the moving vector V from a movement of endoscope 2 as illustrated in FIG. 5. The scene information acquisition unit 12 may acquire the moving vector V by using any method other than these methods.

In the method of FIG. 4A, the moving vector V is detected from two or more endoscope images B at different times. Specifically, the moving vector V is calculated from the equation below.

$$V = P1 - P2$$

P1 is the three-dimensional position vector (x1,y1,z1) of the tip 6*a* in the endoscope image B at time t, and P2 is the three-dimensional position vector (x2,y2,z2) of the tip 6*a* in the endoscope image B at time t+Δt, that is, after a lapse of Δt from time t. The endoscope image B is inputted to the controller 1 directly from the endoscope 2 or through the endoscope processor 4.

In the method of FIG. 5, the moving vector V is detected from a movement of the endoscope 2 that follows the surgical instrument 6. Specifically, the endoscope 2 follows the surgical instrument 6 such that the tip 6*a* of the surgical instrument 6 and the tip 2*b* of the endoscope 2 keep a predetermined positional relationship, so that the movement of the tip 2*b* of the endoscope 2 keeps a fixed relationship with the movement of the tip 6*a* of the surgical instrument 6.

The offset parameter determination unit 13 determines an offset parameter on the basis of the moving vector V. The offset parameter is a parameter that determines the position of the target point T with respect to the fiducial point O and indicates, for example, the offset direction and the offset distance of the target point T with respect to the fiducial point O.

Figure 6A:
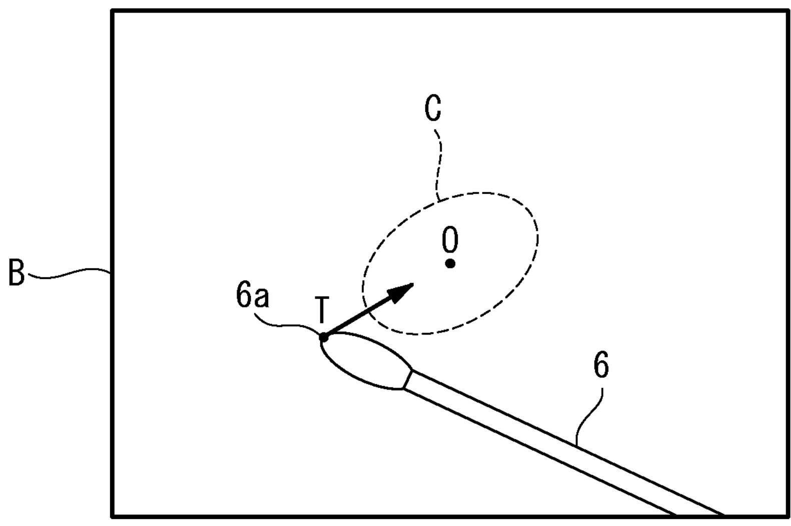
FIG. 6A illustrates an example of an endoscope image in an ablating scene.
Figure 6B:
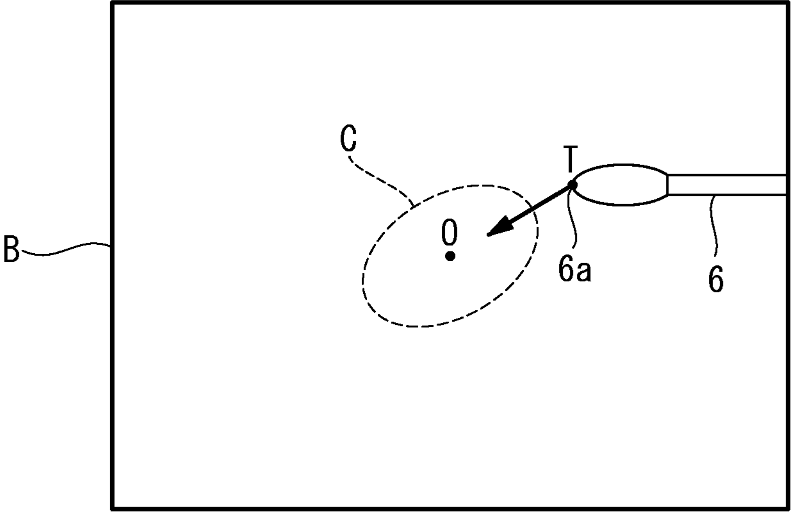
FIG. 6B illustrates another example of an endoscope image in the ablating scene.

Specifically, as illustrated in FIGS. 6A and 6B, the offset parameter determination unit 13 determines an offset parameter that causes a region C ahead of the surgical instrument 6 in the moving direction of the surgical instrument 6 to lie at the center of the field of view F (that is, on the optical axis A), on the basis of the direction of the moving vector V. In FIGS. 6A and 6B, arrows indicate the moving directions of the surgical instrument 6.

For example, the offset parameter determination unit 13 calculates a three-dimensional vector in the direction opposite to the moving vector V as an offset parameter by substituting the moving vector V into a predetermined function F(V). The magnitude of the three-dimensional vector may be fixed or may be determined according to the magnitude of the moving vector V.

Figure 4B:
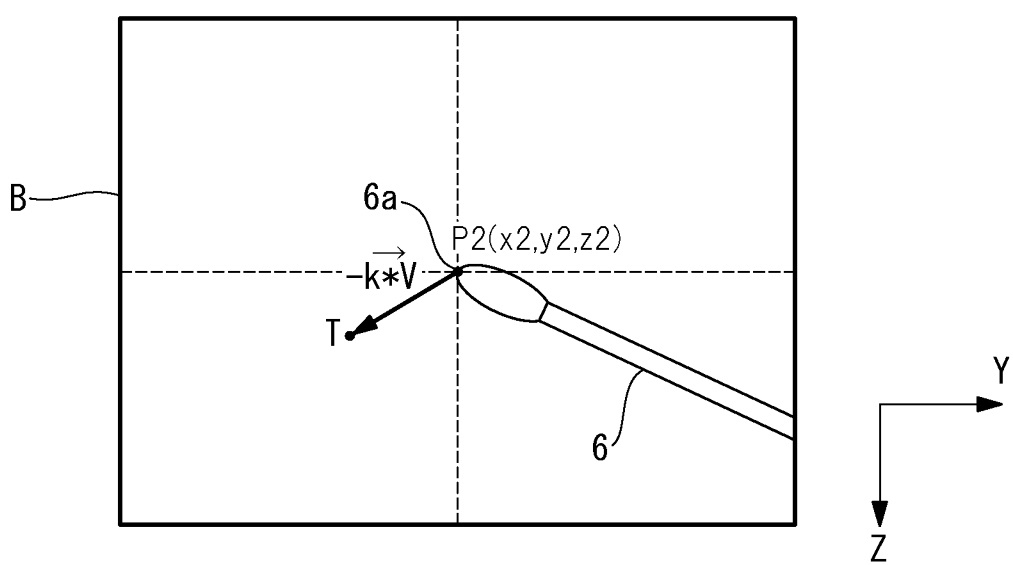
FIG. 4B is an explanatory drawing of an offset parameter determined from the moving vector of FIG. 4A and the target point.

For example, as illustrated in FIG. 4B, F(V)=−k*V is determined, where k is a coefficient. In this case, as the moving vector V increases, the three-dimensional vector F(V) increases and the offset distance of the target point T with respect to the fiducial point O also increases.

In this case, the offset parameter determination unit 13 determines whether a magnitude |V| of the moving vector V, that is, the velocity of the surgical instrument 6 is at most a predetermined threshold value α. If |V| is equal to or smaller than the threshold value α, the offset parameter determination unit 13 determines an offset parameter and outputs the offset parameter to the control unit 14. If |V| is larger than the threshold value α, the offset parameter determination unit 13 does not determine an offset parameter.

The control unit 14 calculates, from the offset parameter, the three-dimensional position of the target point T for causing the region C ahead of the surgical instrument 6 in the moving direction to lie at the center of the field of view F.

For example, the control unit 14 calculates a position offset from the fiducial point O by the magnitude of the three-dimensional vector (−k*V) in the direction of the three-dimensional vector (−k*V), as the three-dimensional position of the target point T. The control unit 14 then sets the target point T at the calculated three-dimensional position, thereby offsetting the target point T from the fiducial point O.

Moreover, the control unit 14 receives three-dimensional position information on the tip 6*a* of the surgical instrument 6 from the position information acquisition unit 11.

Subsequently, the control unit 14 calculates the position and orientation of the tip 2*b* of the endoscope 2 such that the target point T is disposed at the three-dimensional position of the tip 6*a*. The control unit 14 then calculates a movement (e.g., a rotation angle of each of the joints 3*b*) of the moving device 3 for placing the tip 2*b* at the calculated position and orientation and operates the moving device 3 according to the calculated movement. Thus, the tip 2*b* of the endoscope 2 follows the tip 6*a* of the surgical instrument 6, and the target point T moves toward the tip 6*a*.

The control method performed by the controller 1 will be described below.

Figure 7:
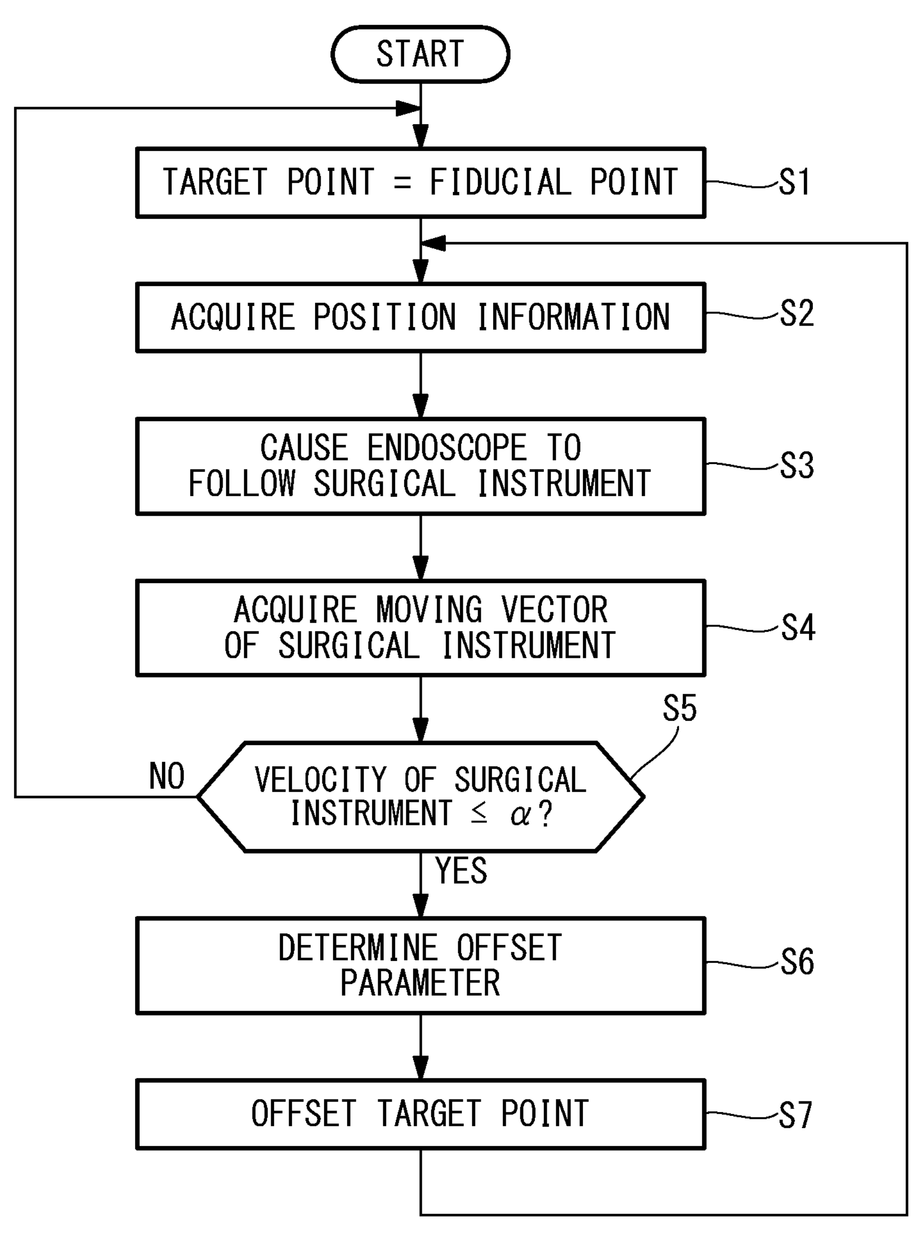
FIG. 7 is a flowchart of a control method according to a first embodiment.

When switching to the follow-up mode, the processor 1*a* of the controller 1 performs steps S1 to S7 in FIG. 7 to cause the endoscope 2 to automatically follow the surgical instrument 6.

At the start of the follow-up mode, the control unit 14 initially sets the target point T at the fiducial point O at the center of the field of view F of the endoscope 2 (step S1).

Subsequently, the position information acquisition unit 11 acquires position information including the three-dimensional position of the tip 6*a* of the surgical instrument 6 (step S2).

The control unit 14 then causes the tip 2*b* of the endoscope 2 to follow the tip 6*a* of the surgical instrument 6 such that the tip 6*a* is disposed at the target point T (step S3). Specifically, the control unit 14 controls the moving device 3 on the basis of the three-dimensional positions of the tip 6*a* and the target point T and moves the endoscope 2 such that the target point T in the field of view F is disposed at the position of the tip 6*a*.

The processing of steps S4 to S7 for adjusting the position of the target point T is performed in parallel with the control for causing the endoscope 2 to follow the surgical instrument 6.

First, the scene information acquisition unit 12 acquires the moving vector V of the surgical instrument 6 (step S4).

If the magnitude |V| of the moving vector is larger than the threshold value α (NO at step S5), the processing of steps S6 and S7 is not performed and the control unit 14 keeps the target point T at the fiducial point O (step S1). Thus, the endoscope 2 follows the surgical instrument 6 such that the tip 6*a* is disposed at the center of the endoscope image B.

If the magnitude |V| of the moving vector is equal to or smaller than the threshold value α (YES at step S5), the offset parameter determination unit 13 determines an offset parameter that causes the region C ahead of the surgical instrument 6 in the moving direction to lie at the fiducial point O, on the basis of the moving vector V (step S6). The control unit 14 then sets, on the basis of the offset parameter, the target point T at a position offset from the fiducial point O in the direction opposite to the moving vector V (step S7). Thus, the endoscope 2 follows the surgical instrument 6 such that the tip 6*a* of the surgical instrument 6 is disposed at the target point T offset from the center of the endoscope image B.

When a biological tissue is ablated by the surgical instrument 6, the surgeon slowly moves the surgical instrument 6 and thus the velocity |V| of the surgical instrument 6 decreases. Thus, as illustrated in FIG. 6A or 6B, when the surgeon starts ablating with the surgical instrument 6, the target point T is offset from the fiducial point O at the center of the field of view F in the direction opposite to the moving direction of the surgical instrument 6, so that the tip 6*a* is offset from the center of the endoscope image B in the direction opposite to the ablating direction and the region C to be ablated is disposed at the center of the endoscope image B. When the ablating is completed and the velocity of the surgical instrument 6 exceeds the threshold value α, the target point T returns to the fiducial point O and the tip 6*a* is disposed at the center of the endoscope image B.

As described above, a motion of the surgical instrument 6 varies according to a procedure scene. According to the present embodiment, the target point T is three-dimensionally offset from the fiducial point O on the basis of the moving vector of the surgical instrument 6, thereby placing the tip 6*a* of the surgical instrument 6 in the endoscope image B at a position suitable for the current procedure scene.

In the case of, in particular, an ablating scene when the magnitude |V| of the moving vector is equal to or smaller than the threshold value α, the tip 6*a* is disposed at a position offset from the fiducial point O in the direction opposite to the moving direction of the surgical instrument 6, so that the region C ahead of the surgical instrument 6 in the moving direction, that is, the region to be ablated is disposed at the center of the endoscope image B. This allows the surgeon to easily observe the region C to be ablated.

In the present embodiment, the offset parameter determination unit 13 determines an offset parameter by using the function F(V). Instead of the function F(V), a parameter table E in which the moving vector V and an offset parameter are associated with each other may be used to determine the offset parameter.

Figure 8:
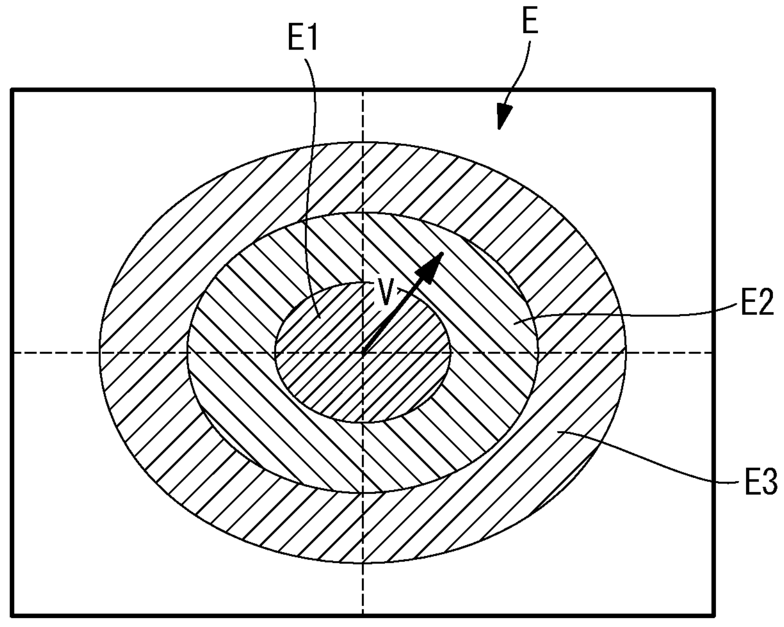
FIG. 8 illustrates an example of a parameter table indicating the correspondence between the moving vector of the surgical instrument and the offset parameter.

FIG. 8 illustrates an example of the parameter table E. In the parameter table E, three regions E1, E2, and E3 for a low speed, a medium speed, and a high speed are set according to the magnitude |V| of the moving vector, and offset distances δ1, δ2, and δ3 are set for the respective regions E1, E2, and E3. For example, the offset distance δ1 of the region E1, the offset distance δ2 of the region E2, and the offset distance δ3 of the region E3 have the relationship of δ1<δ2<δ3. In the case of FIG. 8, |V| corresponds to the region E2 for a medium speed, so that the target point T is disposed at a position offset by the offset distance δ2 from the fiducial point O in the direction opposite to the moving vector V.

Figure 9:
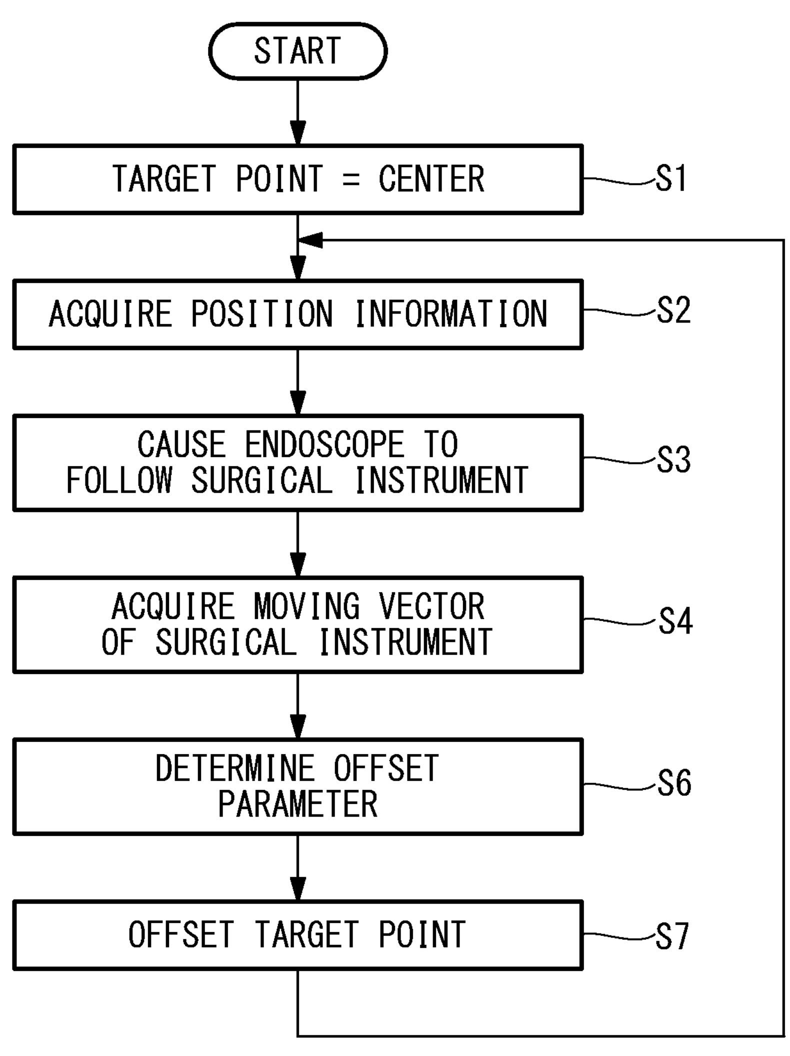
FIG. 9 is a flowchart of a modification of the control method according to the first embodiment.

FIG. 9 illustrates a control method when the parameter table E is used. As indicated in FIG. 9, step S5 is omitted and an offset parameter is repeatedly determined regardless of |V|.

Second Embodiment

A controller, an endoscope system, and a control method according to a second embodiment of the present invention will be described below.

The present embodiment is different from the first embodiment in that an offset parameter is determined on the basis of a moving vector V and the type of a surgical instrument 6. In the present embodiment, configurations different from those of the first embodiment will be described. Configurations in common with the first embodiment are indicated by the same reference numerals and an explanation thereof is omitted.

An endoscope system 10 according to the present embodiment includes a controller 1, an endoscope 2, a moving device 3, an endoscope processor 4, and a display device 5.

Figure 10:
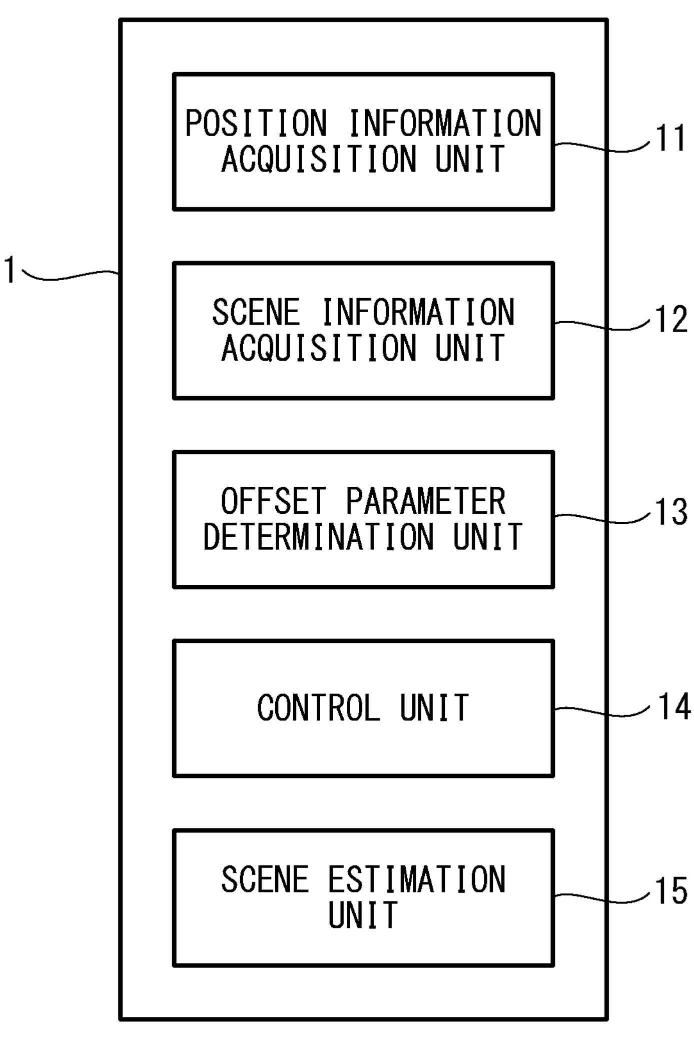
FIG. 10 is a functional block diagram illustrating a controller for an endoscope system according to a second embodiment.

As illustrated in FIG. 10, the controller 1 further includes a scene estimation unit 15 in addition to a position information acquisition unit 11, a scene information acquisition unit 12, an offset parameter determination unit 13, and a control unit 14. The function of the scene estimation unit 15 is implemented by a processor 1*a* as the other units 11, 12, 13, and 14.

The scene information acquisition unit 12 acquires the type of the surgical instrument 6 set to be followed, as scene information in addition to the moving vector V. For example, the scene information acquisition unit 12 acquires the type of the surgical instrument from an endoscope image B by recognizing the type of the surgical instrument 6 in the endoscope image B through AI image recognition. The scene information acquisition unit 12 may acquire the type of the surgical instrument 6 on the basis of information on the type of the surgical instrument 6 when the type is inputted to the controller 1 by an operator, or identification information or the like provided for the surgical instrument 6.

The scene estimation unit 15 estimates a procedure scene observed through the endoscope 2, on the basis of the type of the surgical instrument 6. Specifically, when the type of the surgical instrument 6 is an unfolding device, e.g., gripping forceps, the scene estimation unit 15 estimates that the procedure scene is an unfolding scene of unfolding a biological tissue by using the surgical instrument 6. When the type of the surgical instrument 6 is an ablating device, e.g., an electrosurgical knife, the scene estimation unit 15 estimates that the procedure scene is an ablating scene of ablating a biological tissue by using the surgical instrument 6.

The offset parameter determination unit 13 determines an offset parameter on the basis of the moving vector V and the procedure scene.

Specifically, as illustrated in FIGS. 6A and 6B, when the procedure scene is an ablating scene, the offset parameter determination unit 13 determines an offset parameter that causes a region C to be ablated by the surgical instrument 6, that is, the region C ahead of the surgical instrument 6 in the moving direction of the surgical instrument 6 to lie at the center of a field of view F.

Figure 11:
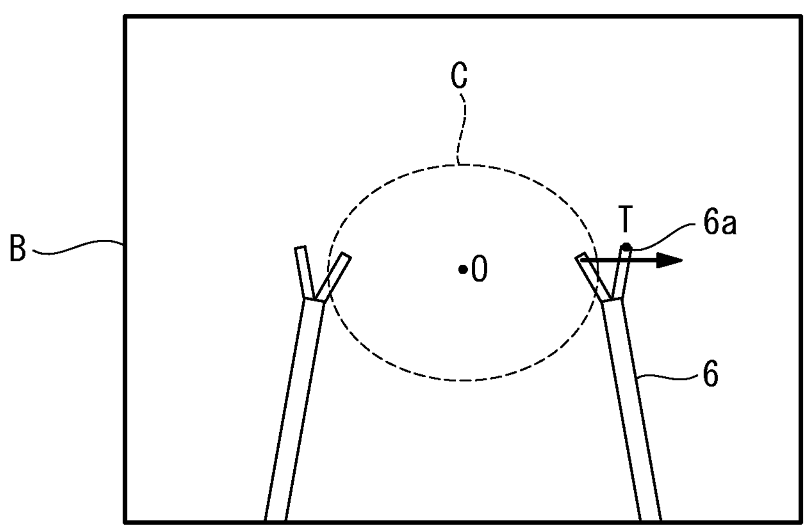
FIG. 11 illustrates an example of an endoscope image in an unfolding scene.

If the procedure scene is an unfolding scene, as illustrated in FIG. 11, the offset parameter determination unit 13 determines an offset parameter that causes the region C to be unfolded by the surgical instrument 6, that is, the region C behind the surgical instrument 6 in the moving direction of the surgical instrument 6 to lie at the center of the field of view F.

For example, a function F(V) or a parameter table E is prepared in advance for each procedure scene and is stored in a storage unit 1*c*. In the case of the ablating scene, the offset parameter determination unit 13 selects the function F(V) or the parameter table E for the ablating scene and calculates, as an offset parameter, a three-dimensional vector in the direction opposite to the moving vector V by using the selected function F(V) or the parameter table E. In the case of the unfolding scene, the offset parameter determination unit 13 selects the function F(V) or the parameter table E for the unfolding scene and calculates, as an offset parameter, a three-dimensional vector in the same direction as the moving vector V by using the selected function F(V) or the parameter table E.

The control method performed by the controller 1 will be described below.

Figure 12:
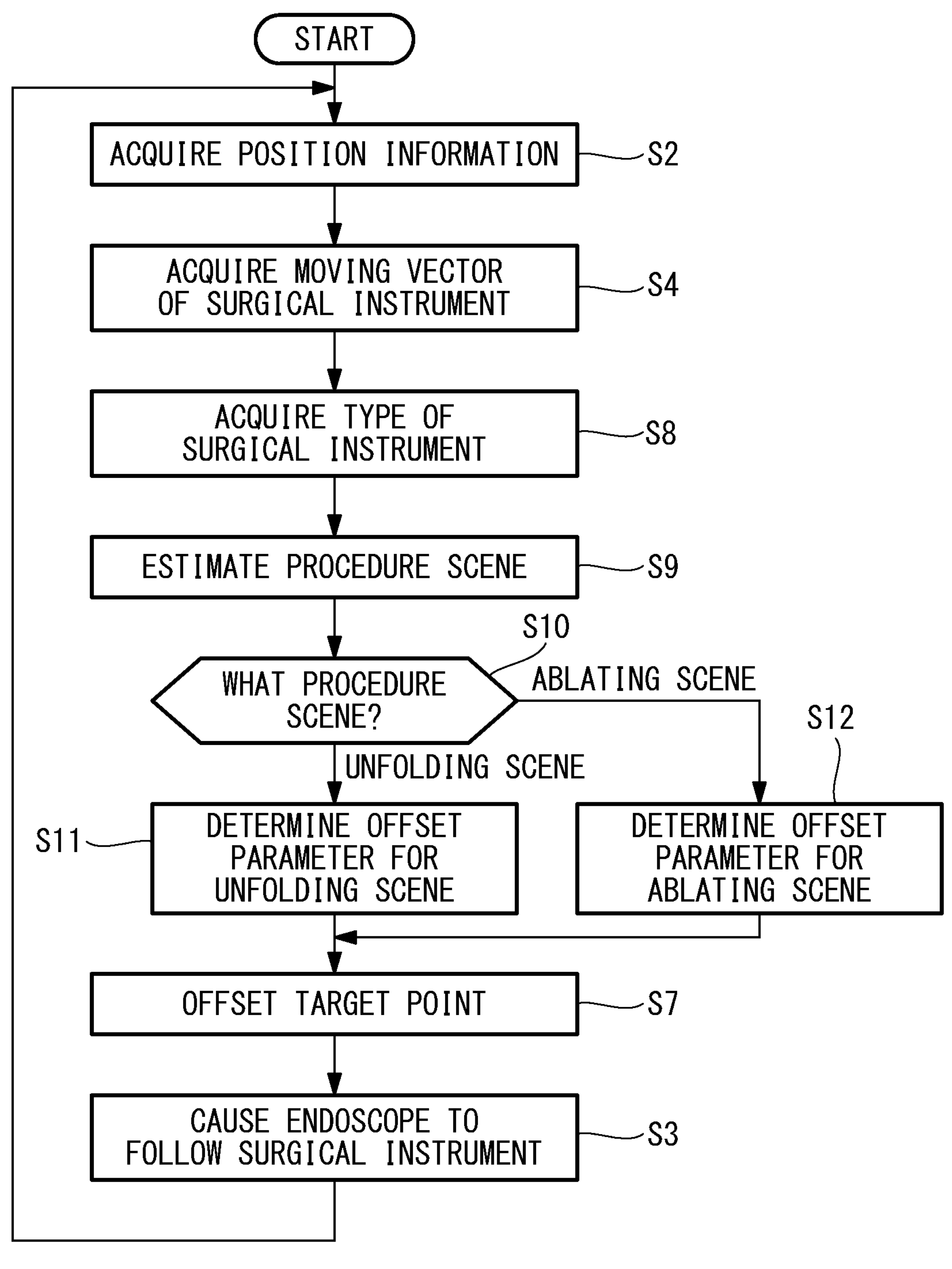
FIG. 12 is a flowchart of a control method according to a second embodiment.

When switching to the follow-up mode, the processor 1*a* of the controller 1 performs steps S2 to S12 in FIG. 12 to cause the endoscope 2 to automatically follow the surgical instrument 6 to be followed.

In the present embodiment, the scene information acquisition unit 12 acquires the moving vector V (step S4) and acquires the type of the surgical instrument 6 (step S8).

The scene estimation unit 15 then estimates a procedure scene observed through the endoscope 2, on the basis of the type of the surgical instrument 6 (step S9).

The offset parameter determination unit 13 then determines an offset parameter on the basis of the procedure scene and the moving vector V (steps S10 to S12).

Specifically, in the case of the unfolding scene ("unfolding scene" in step S10), the offset parameter determination unit 13 calculates an offset parameter by using the function F(V) or the parameter table E for the unfolding scene (step S11). Thus, as illustrated in FIG. 11, a target point T is offset from a fiducial point O at the center of the field of view F in the same direction as the moving direction of the surgical instrument 6, a tip 6*a* of the surgical instrument 6 is offset from the center of the endoscope image B in the same direction as the unfolding direction, and the region C to be unfolded by the surgical instrument 6 is disposed at the center of the endoscope image B.

In the case of the ablating scene ("ablating scene" in step S10), the offset parameter determination unit 13 calculates an offset parameter by using the function F(V) or the parameter table E for the ablating scene (step S12). Thus, as illustrated in FIGS. 6A and 6B, the target point T is offset from the center of the field of view F in the direction opposite to the moving direction of the surgical instrument 6, the tip 6*a* of the surgical instrument 6 is offset from the center of the endoscope image B in the direction opposite to the ablating direction, and the region C to be ablated by the surgical Instrument 6 is disposed at the center of the endoscope image B.

During a surgical operation, various procedure scenes can be observed through the endoscope 2. The type of the used surgical instrument 6 varies according to a procedure scene. According to the present embodiment, the current procedure scene is estimated on the basis of the type of the surgical instrument 6, and the target point T is three-dimensionally offset from the fiducial point O on the basis of the moving vector V and the procedure scene. Thus, the tip 6*a* of the surgical instrument 6 in the endoscope image B can be disposed at a position suitable for the current procedure scene.

Specifically, in the unfolding scene, the region C unfolded by the surgical instrument 6 is disposed at the center of the endoscope image B, allowing a surgeon to easily observe the unfolded region C. In the ablating scene, the region C to be ablated by the surgical instrument 6 is disposed at the center of the endoscope image B, allowing the surgeon to easily observe the region C to be ablated.

The scene information acquisition unit 12 may acquire any other kind of information recognizable by AI, instead of the type of the surgical instrument 6.

For example, the scene information acquisition unit 12 may recognize the anatomical characteristics of a subject in the endoscope image B according to a known image recognition technique and acquire information including the kinds of the anatomical characteristics, positions, and orientations as scene information, and the scene estimation unit 15 may estimate a procedure scene on the basis of the scene information.

Alternatively, the scene information acquisition unit 12 may detect a change of a scene, e.g., bleeding of a subject in the endoscope image B according to a known image recognition technique and acquire the detected information as scene information, and the scene estimation unit 15 may estimate a procedure scene on the basis of the scene information.

Scene estimation is not limited to the foregoing embodiments. The scene information acquisition unit 12 can acquire, as scene information, any kind of information obtained in a surgical operation, and the scene estimation unit 15 may estimate a procedure scene on the basis of the scene information.

Third Embodiment

A controller, an endoscope system, and a control method according to a third embodiment of the present invention will be described below.

The present embodiment is different from the first and second embodiments in that an offset parameter is determined on the basis of a moving vector V and the type and the operating state of a surgical instrument 6. In the present embodiment, configurations different from those of the first and second embodiments will be described. Configurations in common with the first and second embodiments are indicated by the same reference numerals and an explanation thereof is omitted.

An endoscope system 10 according to the present embodiment includes a controller 1, an endoscope 2, a moving device 3, an endoscope processor 4, and a display device 5.

As in the second embodiment, the controller 1 includes a position information acquisition unit 11, a scene information acquisition unit 12, an offset parameter determination unit 13, a control unit 14, and a scene estimation unit 15.

The scene information acquisition unit 12 acquires the operating state of the surgical instrument 6 to be followed, as scene information in addition to the moving vector V and the type of the surgical instrument 6. For example, the controller 1 is connected to a drive unit (not illustrated) for driving the surgical instrument 6. The surgical instrument 6 is activated by power supply from the drive unit. The scene information acquisition unit 12 receives a signal indicating whether the surgical instrument 6 is active or inactive from the drive unit.

The scene information acquisition unit 12 may acquire an operating state by using another means. For example, the scene information acquisition unit 12 may acquire the operating state of the surgical instrument 6 from an endoscope image B. When the surgical instrument 6 is an electrosurgical knife, the color of the electrosurgical knife 6 in an active state is changed by high heat unlike in an inactive state. Thus, whether the surgical instrument 6 is active or inactive can be recognized from the endoscope image B.

As in the second embodiment, the scene estimation unit 15 estimates a procedure scene on the basis of the type of the surgical instrument 6. When the procedure scene is estimated to be an ablating scene, the scene estimation unit 15 estimates a more specific procedure scene on the basis of the operating state of the surgical instrument 6. Specifically, when the surgical instrument 6 is active, the scene estimation unit 15 estimates that the surgical instrument 6 is placed in an active scene, that is, a biological tissue is being ablated by the surgical instrument 6. When the surgical instrument 6 is inactive, the scene estimation unit 15 estimates that the surgical instrument 6 is placed in an inactive scene, that is, another scene in the ablating scene.

The offset parameter determination unit 13 determines an offset parameter on the basis of the moving vector V and the procedure scene.

For example, as in the second embodiment, a function F(V) or a parameter table E is prepared in advance for each procedure scene and is stored in a storage unit 1*c*. Specifically, a function F(V) or a parameter table E for an unfolding scene, a function F(V) or a parameter table E for an ablating scene (active), and a function F(V) or a parameter table E for an ablating scene (inactive) are prepared. The offset parameter determination unit 13 selects the function F(V) or the parameter table E for a procedure scene estimated by the scene estimation unit 15 and calculates, as an offset parameter, a three-dimensional vector by using the selected function F(V) or parameter table E.

The control method performed by the controller 1 will be described below.

Figure 13:
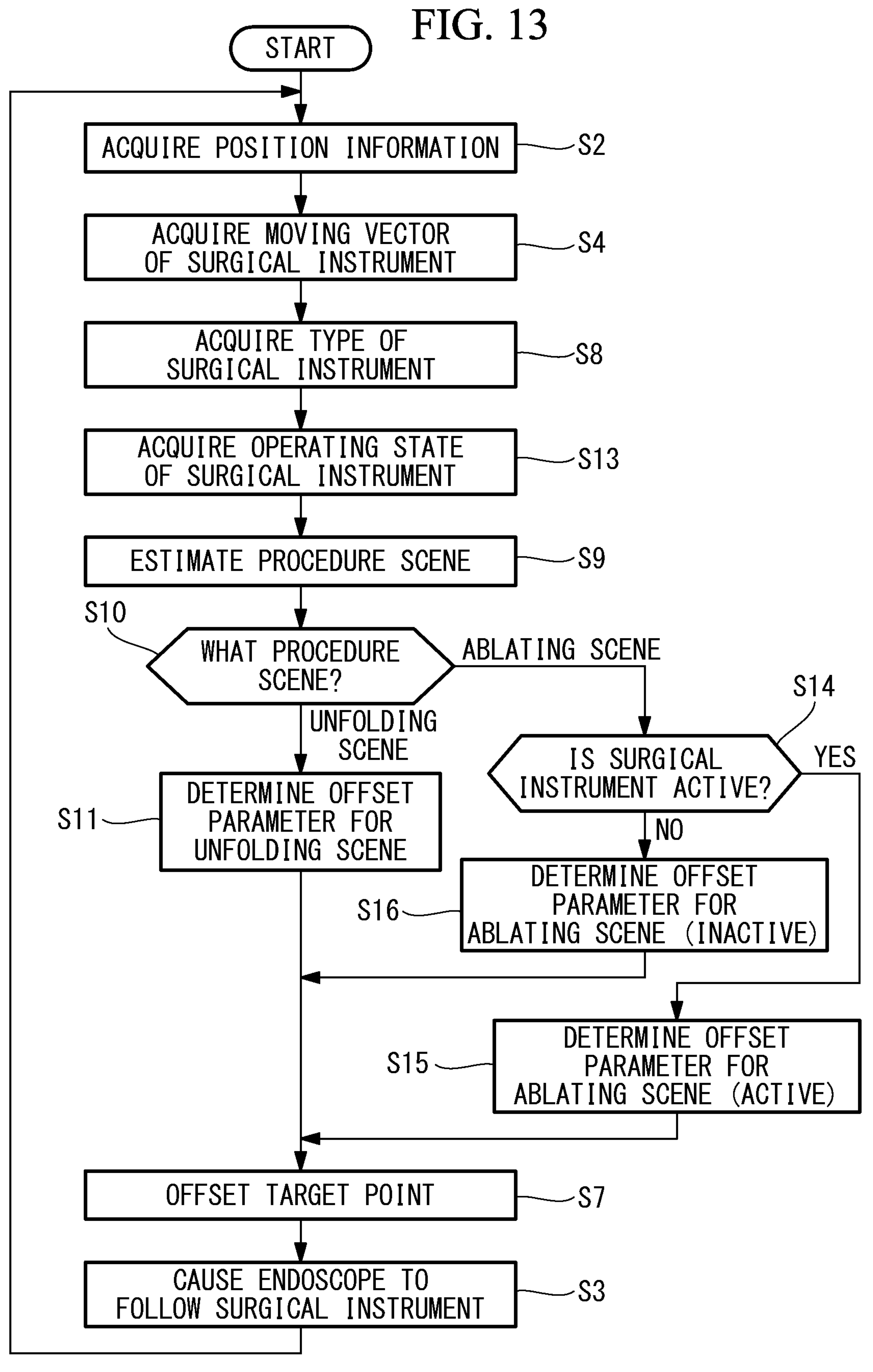
FIG. 13 is a flowchart of a control method according to a third embodiment.

When switching to the follow-up mode, a processor 1*a* of the controller 1 performs steps S2 to S16 in FIG. 13 to cause the endoscope 2 to automatically follow the surgical instrument 6 to be followed.

In the present embodiment, the scene information acquisition unit 12 acquires the moving vector V (step S8), acquires the type of the surgical instrument 6 and acquires the operating state of the surgical instrument 6 (step S13).

The scene estimation unit 15 then estimates a procedure scene observed through the endoscope 2, on the basis of the type of the surgical instrument 6 (step S9). When the procedure scene is an ablating scene ("ablating scene" in step S10), the scene estimation unit 15 then estimates whether the procedure scene is an active scene or an inactive scene of the surgical instrument 6 in the ablating scene, on the basis of the operating state of the surgical instrument 6 (step S14).

The offset parameter determination unit 13 then determines an offset parameter on the basis of the procedure scene and the moving vector V (steps S11, S15, S16).

Specifically, in the case of the unfolding scene ("unfolding scene" in step S10), the offset parameter determination unit 13 calculates an offset parameter by using the function F(V) or the parameter table E for the unfolding scene as in the second embodiment (step S11).

In the ablating scene, when the surgical instrument 6 is placed in an active scene (YES at step S14), the offset parameter determination unit 13 calculates an offset parameter by using the function F(V) or the parameter table E for the ablating scene (active) (step S15).

In the ablating scene, when the surgical instrument 6 is placed in an inactive scene (NO at step S14), the offset parameter determination unit 13 calculates an offset parameter by using the function F(V) or the parameter table E for the ablating scene (inactive) (step S16).

A plurality of scenes may be present in one kind of procedure scene and change during the use of the same surgical instrument 6. For example, the ablating scene includes a scene in which the inactive electrosurgical knife 6 is moved to be aligned with a biological tissue before the start of ablating, a scene in which the active electrosurgical knife 6 is slowly moved to ablate the biological tissue during ablating, and a scene in which the inactive electrosurgical knife 6 is moved to be separated from the biological tissue after the completion of ablating.

According to the present embodiment, the current procedure scene can be more specifically estimated on the basis of the type and the operating state of the surgical instrument 6, and a tip 6*a* of the surgical instrument 6 in the endoscope image B can be disposed at a more suitable position for the current procedure scene.

Fourth Embodiment

A controller, an endoscope system, and a control method according to a fourth embodiment of the present invention will be described below.

The present embodiment is different from the first to third embodiments in that an offset parameter is determined on the basis of a moving vector V and anatomy information on a biological tissue. In the present embodiment, configurations different from those of the first to third embodiments will be described. Configurations in common with the first to third embodiments are indicated by the same reference numerals and an explanation thereof is omitted.

An endoscope system 10 according to the present embodiment includes a controller 1, an endoscope 2, a moving device 3, an endoscope processor 4, and a display device 5.

As in the second embodiment, the controller 1 includes a position information acquisition unit 11, a scene information acquisition unit 12, an offset parameter determination unit 13, a control unit 14, and a scene estimation unit 15.

Figure 14A:
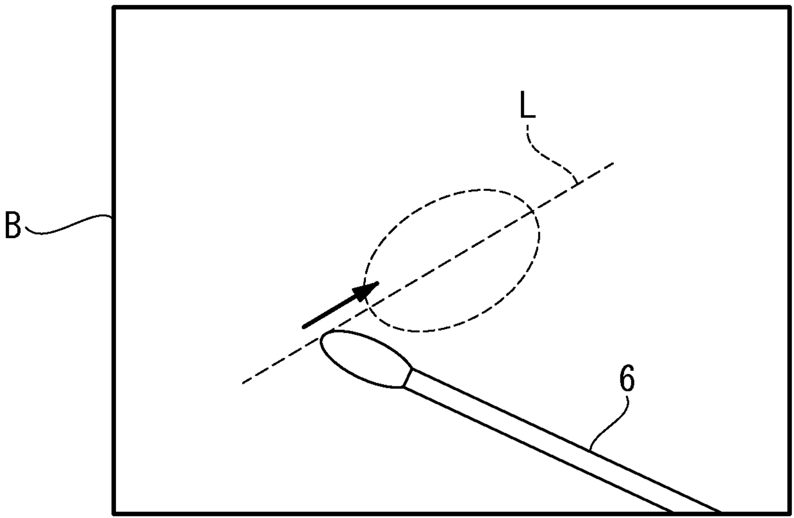
FIG. 14A illustrates an example of an endoscope image for explaining an ablating line and a surgical instrument.
Figure 14B:
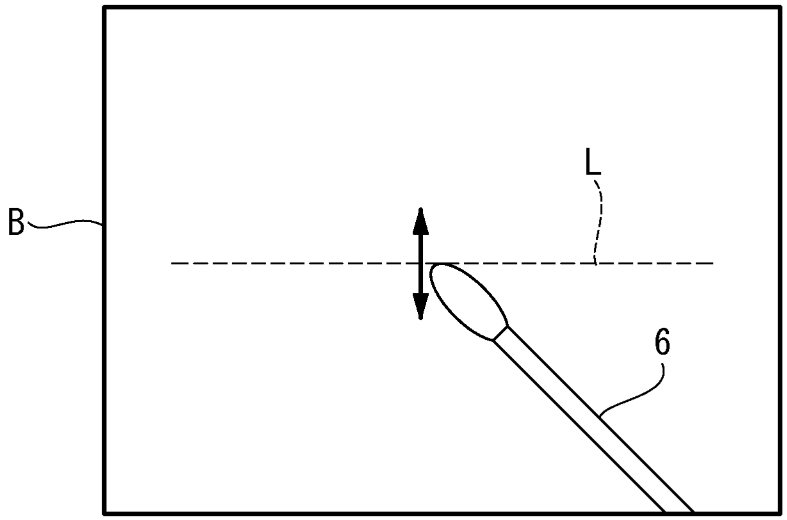
FIG. 14B illustrates another example of an endoscope image for explaining the ablating line and the surgical instrument.

The scene information acquisition unit 12 acquires anatomy information on a biological tissue in an endoscope image B, as scene information in addition to the moving vector V. The anatomy information is information on the anatomical structure of a biological tissue associated with a procedure performed by a surgical instrument 6. For example, the anatomy information is acquired by using an image recognition technique by AI. For example, as illustrated in FIGS. 14A and 14B, the scene information acquisition unit 12 recognizes the layout of organs and blood vessels or the like in the endoscope image B and recognizes, as anatomy information, an ablating line L to be ablated by the surgical instrument 6. When a marking representing the ablating line L is provided on the surface of a biological tissue, the scene information acquisition unit 12 may recognize the marking.

The scene estimation unit 15 estimates a procedure scene on the basis of the moving vector V and the anatomy information.

Specifically, as illustrated in FIG. 14A, when a biological tissue is ablated by the surgical instrument 6, a surgeon moves the surgical instrument 6 along the ablating line L, so that the moving direction of the surgical instrument 6 agrees with the longitudinal direction of the ablating line L. When the direction of the moving vector V agrees with the longitudinal direction of the ablating line L, the scene estimation unit 15 estimates that the procedure scene is an ablating scene of ablating a biological tissue by using the surgical instrument 6.

As illustrated in FIG. 14B, when the surgical instrument 6 performs an operation other than ablating, for example, when the surgical instrument 6 is moved in a direction that crosses the ablating line L and unfolds an ablated portion, the moving direction of the surgical instrument 6 does not agree with the longitudinal direction of the ablating line L. When the direction of the moving vector V does not agree with the longitudinal direction of the ablating line L, the scene estimation unit 15 estimates that the procedure scene is a scene other than an ablating scene.

Whether the direction of the moving vector V agrees with the longitudinal direction of the ablating line L is determined depending upon, for example, whether an angle formed by the direction of the moving vector V and the direction of the ablating line L is at most a predetermined value.

The offset parameter determination unit 13 determines an offset parameter on the basis of the moving vector V and the procedure scene.

Specifically, when the procedure scene is an ablating scene, the offset parameter determination unit 13 determines an offset parameter that causes a region C ahead of the surgical instrument 6 in the moving direction of the surgical instrument 6 to lie at the center of a field of view F.

If the procedure scene is a scene other than an ablating scene, the offset parameter determination unit 13 determines an offset parameter that places a target point T at a fiducial point O.

The control method performed by the controller 1 will be described below.

Figure 15:
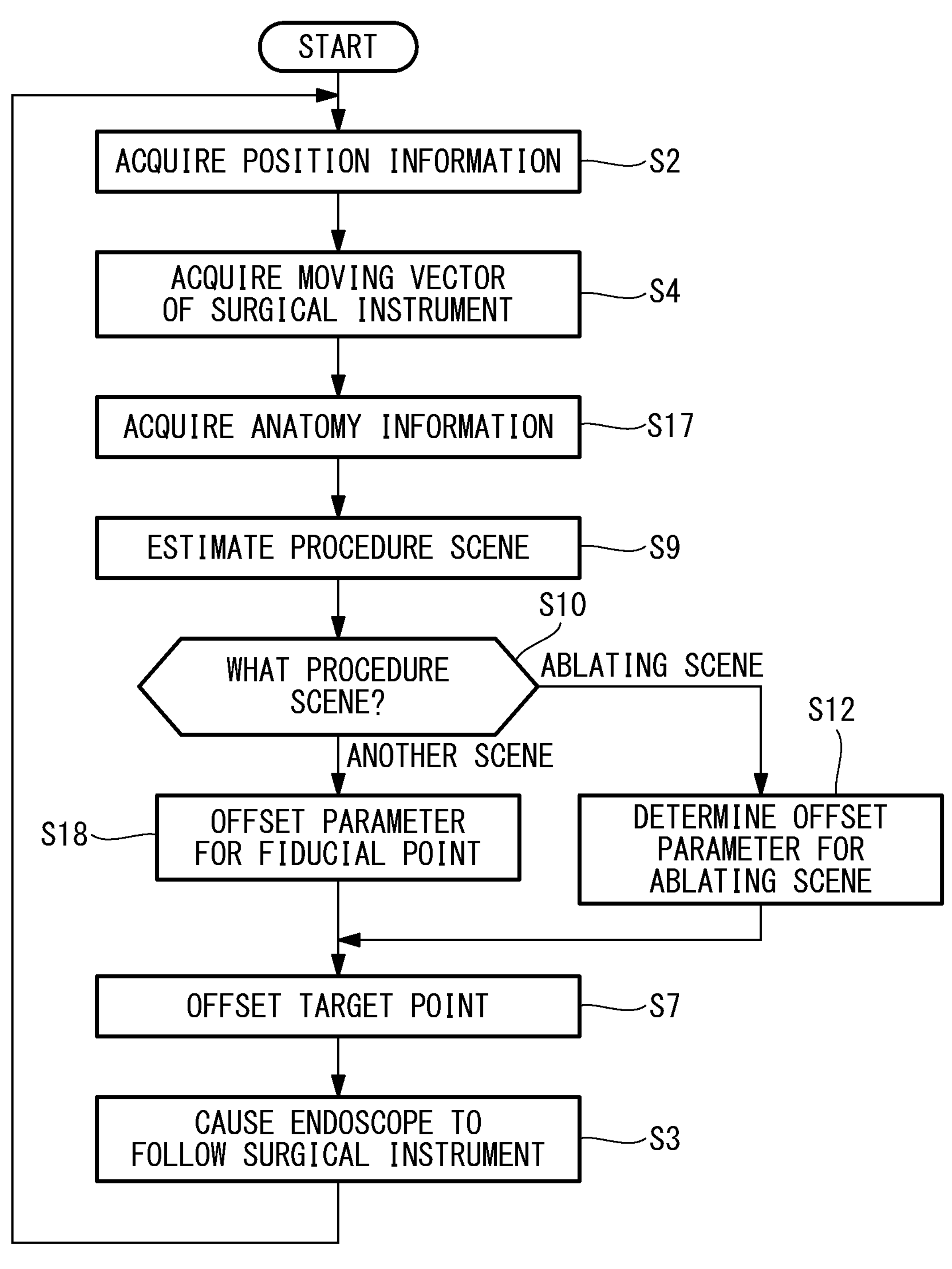
FIG. 15 is a flowchart of a control method according to a fourth embodiment.

When switching to a follow-up mode, a processor 1*a* of the controller 1 performs steps S2 to S18 in FIG. 15 to cause the endoscope 2 to automatically follow the surgical instrument 6 to be followed.

In the present embodiment, the scene information acquisition unit 12 acquires the moving vector V (step S4) and acquires anatomy information in the endoscope image B (step S17).

The scene estimation unit 15 then estimates a procedure scene observed through the endoscope 2, on the basis of the moving vector V and the anatomy information (step S9). Specifically, when the direction of the moving vector V agrees with the longitudinal direction of the ablating line L, the scene estimation unit 15 estimates that the procedure scene is an ablating scene. When the direction of the moving vector V does not agree with the longitudinal direction of the ablating line L, the scene estimation unit 15 estimates that the procedure scene is another scene.

The offset parameter determination unit 13 then determines an offset parameter on the basis of the procedure scene and the moving vector V (steps S10, S12, S18).

Specifically, in the case of the ablating scene ("ablating scene" in step S10), the offset parameter determination unit 13 calculates an offset parameter by using the function F(V) or a parameter table E for the ablating scene (step S12). Thus, the target point T is offset from the center of the field of view F in the direction opposite to the moving direction of the surgical instrument 6 (step S7), a tip 6*a* of the surgical instrument 6 is offset from the center of the endoscope image B in the direction opposite to the ablating direction, and the region C to be ablated by the surgical instrument 6 is disposed at the center of the endoscope image B.

In the case of another scene ("another scene" in step S10), the offset parameter determination unit 13 determines an offset parameter that places the target point T at the fiducial point O (step S18). Thus, the target point T is set at the center of the field of view F, and the tip 6*a* of the surgical instrument 6 is disposed at the center of the endoscope image B.

As described above, the present embodiment can estimate the current procedure scene on the basis of the anatomy information in the endoscope image B and the moving vector V representing a motion of the surgical instrument 6. Moreover, the tip 6*a* of the surgical instrument 6 in the endoscope image B can be disposed at a position suitable for the current procedure scene by determining whether the target point T is to be offset from the fiducial point O on the basis of the procedure scene.

Specifically, in the ablating scene where a surgeon moves the surgical instrument 6 along the ablating line L, the region C to be ablated by the surgical instrument 6 is disposed at the center of the endoscope image B, allowing the surgeon to easily observe the region C to be ablated.

In a scene other than the ablating scene, the target point T is set at the fiducial point O, and the tip 6*a* of the surgical instrument 6 is disposed at the center of the endoscope image B. This allows the surgeon to easily observe the tip 6*a* of the surgical instrument 6.

In the present embodiment, the type of the surgical instrument 6 according to the second embodiment may be further used as the scene information. When the procedure scene is estimated to be another scene on the basis of the moving vector V and the anatomy information, the procedure scene may be then estimated on the basis of the type of the surgical instrument 6.

In the present embodiment, the type and the operating state of the surgical instrument 6 according to the third embodiment may be further used as the scene information. For example, when the procedure scene is estimated to be another scene on the basis of the moving vector and the anatomy information, the procedure scene may be then estimated on the basis of the type and the operating state of the surgical instrument 6.

Fifth Embodiment

A controller, an endoscope system, and a control method according to a fifth embodiment of the present invention will be described below.

The present embodiment is different from the first to fourth embodiments in that an offset parameter is determined on the basis of an input of an operator. In the present embodiment, configurations different from those of the first to fourth embodiments will be described. Configurations in common with the first to fourth embodiments are indicated by the same reference numerals and an explanation thereof is omitted.

An endoscope system 10 according to the present embodiment includes a controller 1, an endoscope 2, a moving device 3, an endoscope processor 4, and a display device 5.

As in the first embodiment, the controller 1 includes a position information acquisition unit 11, a scene information acquisition unit 12, an offset parameter determination unit 13, and a control unit 14.

A user interface 1*d* includes any input device, e.g., a mouse, a keyboard, or a touch panel. An operator can input the position of a tip 6*a* of a surgical instrument 6 to the controller 1 by using the user interface 1*d*.

For example, as illustrated in FIG. 3A, offset angles φy and φz are inputted as the position of the tip 6*a*. The offset angle φy is an angle formed on the XY plane by an optical axis A and a line connecting the positions of a tip 2*b* of the endoscope 2 and a tip 6*a*, and the offset angle φz is an angle formed on the XZ plane by the optical axis A and a line connecting the positions of the tip 2*b* of the endoscope 2 and the tip 6*a*. The offset angle φy determines a distance δy from a fiducial point O to the tip 6*a* in the Y direction at each position in the X direction. The offset angle φz determines a distance δz from the fiducial point O to the tip 6*a* in the Z direction at each position in the X direction.

The scene information acquisition unit 12 acquires the position of the tip 6*a* as scene information, the position being inputted by using the user interface 1*d*.

The offset parameter determination unit 13 determines an offset parameter on the basis of the inputted position of the tip 6*a*. For example, the offset parameter determination unit 13 calculates a three-dimensional position (D,δy,δz) determined by a distance D and the offset angles φy and φz, as offset parameters.

The control unit 14 sets a target point T at the three-dimensional position (D,δy,δz). Thus, the position of the tip 6*a* is set at the target point T, the position being inputted by an operator.

The control method performed by the controller 1 will be described below.

Figure 16:
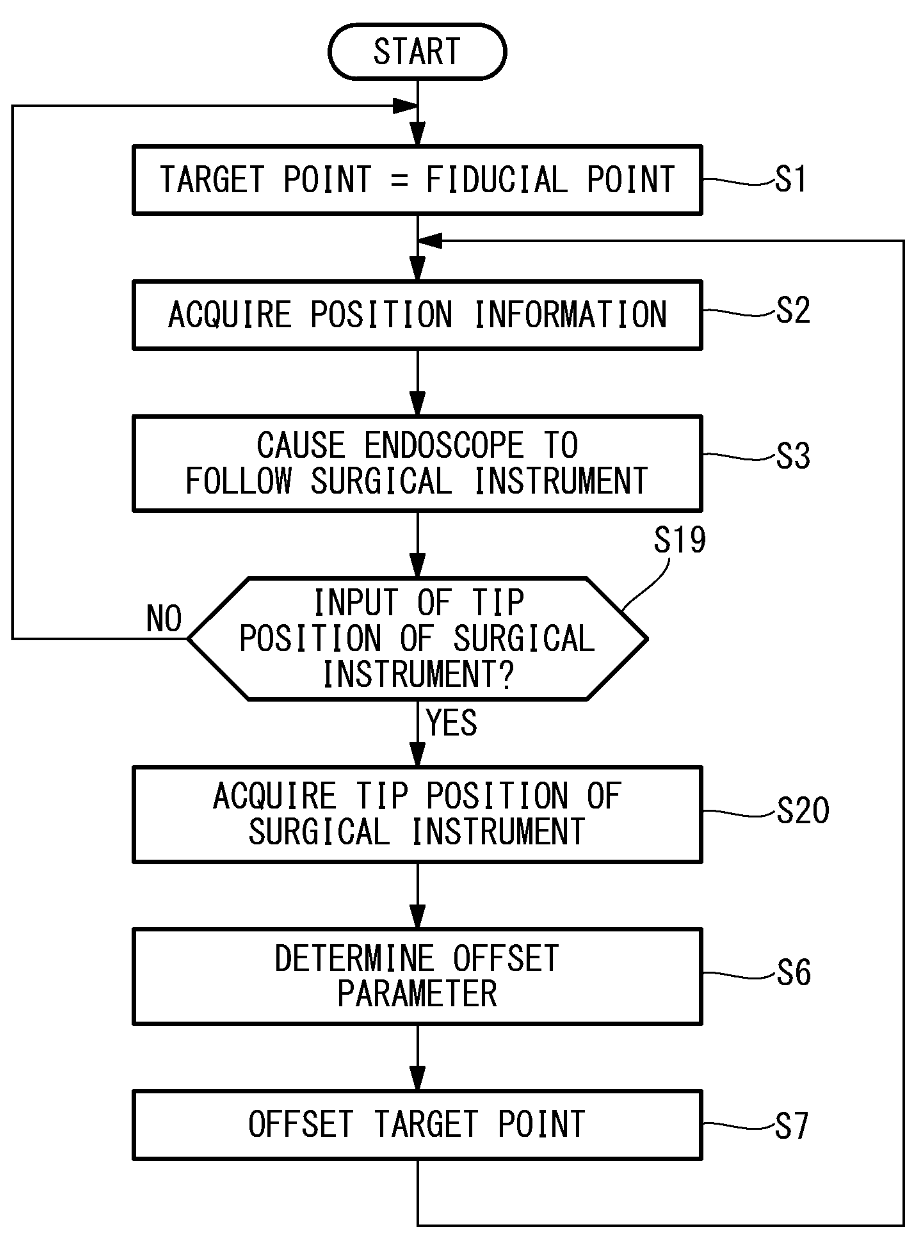
FIG. 16 is a flowchart of a control method according to a fifth embodiment.

When switching to a follow-up mode, a processor 1*a* of the controller 1 performs steps S1 to S20 in FIG. 16 to cause the endoscope 2 to automatically follow the surgical instrument 6 to be followed.

As in the first embodiment, by performing steps S1 to S3, the tip 2*b* of the endoscope 2 follows the tip 6*a* of the surgical instrument 6 such that the tip 6*a* of the surgical instrument 6 is disposed at the fiducial point O in a field of view F.

When the position of the tip 6*a* is to be moved from the center of an endoscope image B to another position according to a procedure scene, an operator inputs a desired position of the tip 6*a* to the controller 1 by using the user interface 1*d*.

When the operator inputs the position of the tip 6*a* to the controller 1 (YES at step S19), the scene information acquisition unit 12 acquires the position inputted by the operator (step S20), the offset parameter determination unit 13 determines an offset parameter on the basis of the inputted position (step S6), and the control unit 14 sets the target point T at the position inputted by the operator (step S7). Thus, the tip 6*a* of the surgical instrument 6 in the endoscope image B is moved from the center to the target point T at the position specified by the operator.

As described above, according to the present embodiment, the input of the position of the tip 6*a* of the surgical instrument 6 by the operator triggers the target point T to be offset to the inputted position. Thus, the operator can set the target point T at any position suitable for the current procedure scene at any time and set the tip 6*a* in the endoscope image B to be offset to any position at any time.

Figure 17:
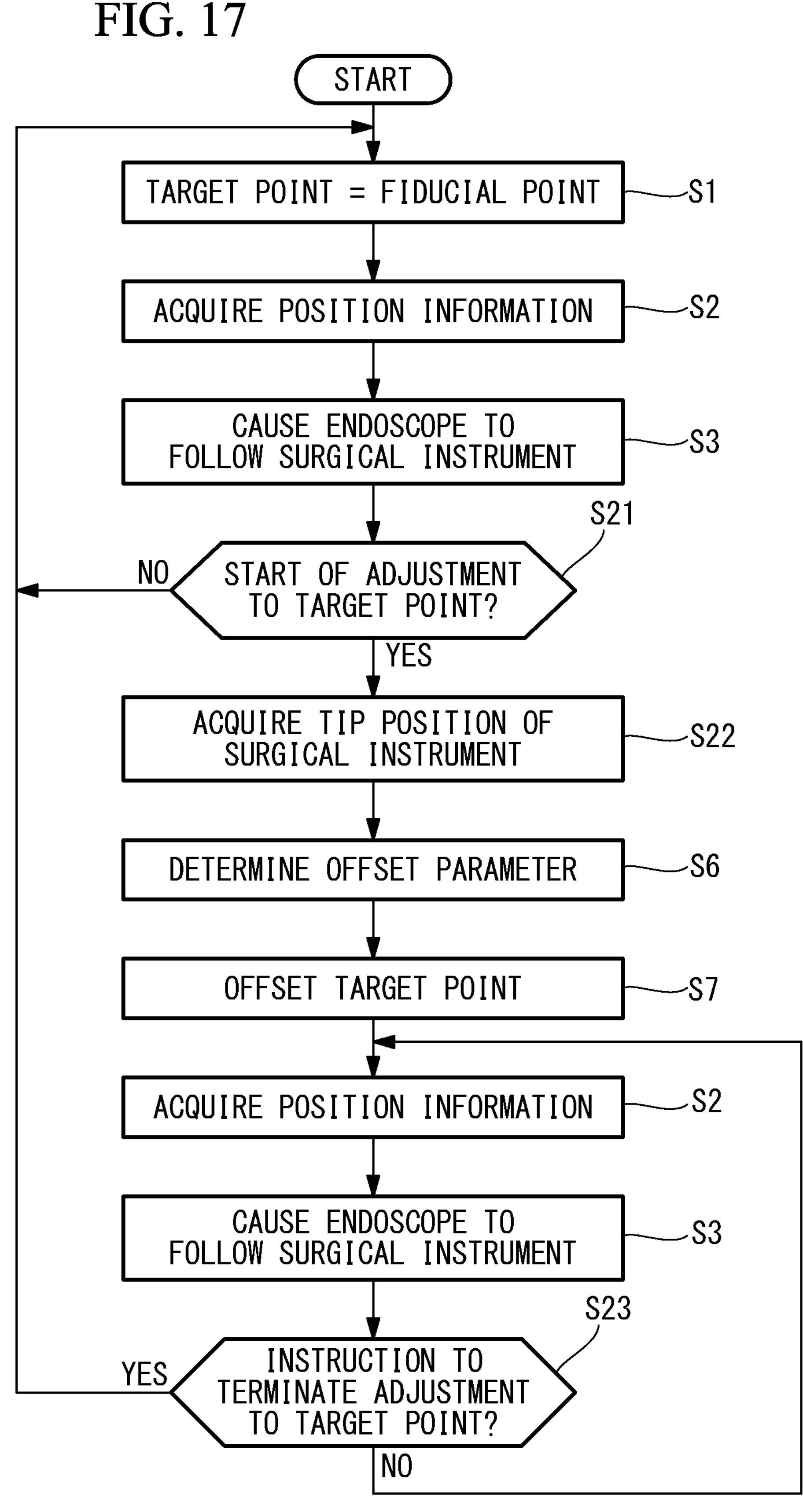
FIG. 17 is a flowchart of a modification of the control method according to the fifth embodiment.

In the present embodiment, as indicated in FIG. 17, the scene information acquisition unit 12 may acquire the position of the tip 6*a* of the surgical instrument 6 as scene information in response to an input of an instruction to start an adjustment to the target point T.

In this case, the operator moves the tip 6*a* of the surgical instrument 6 to a desired position in the endoscope image B and inputs an instruction to start an adjustment to the controller 1 by using the user interface 1*d* (step S21). In response to the input, the scene information acquisition unit 12 acquires the position of the tip 6*a* at the time of the input of the instruction (step S22). For example, the scene information acquisition unit 12 stores the endoscope image B at the time of the input of the instruction and calculates the three-dimensional position of the tip 6*a* of the surgical instrument 6 with respect to the tip 2*b* of the endoscope 2 from the endoscope image B.

When the operator inputs an instruction to terminate the adjustment to the target point T (YES at step S23), the adjustment to the target point T is terminated and the target point T returns to the fiducial point O (step S1).

In the present embodiment, the scene information acquisition unit 12 acquires the position of the tip 6*a* of the surgical instrument 6 as scene information. Alternatively, the position and orientation of the endoscope 2 may be acquired as scene information. For example, the scene information acquisition unit 12 acquires information on the current position and orientation of the endoscope 2 from the moving device 3.

FIGS. 18A to 19B illustrate examples of the position and orientation of the endoscope 2. In laparoscopic surgery, the position and orientation of the endoscope 2 change depending upon the affected part and the details of a procedure, that is, depending upon the procedure scene.

Figure 18A:
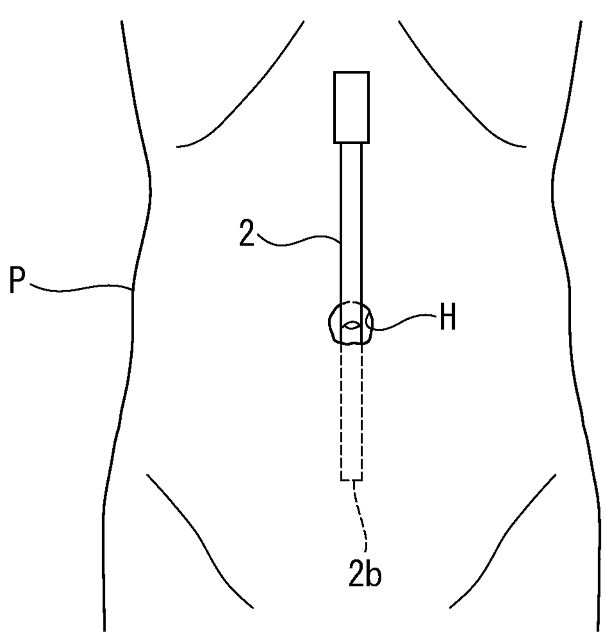
FIG. 18A illustrates an example of the position and orientation of an endoscope.
Figure 18B:
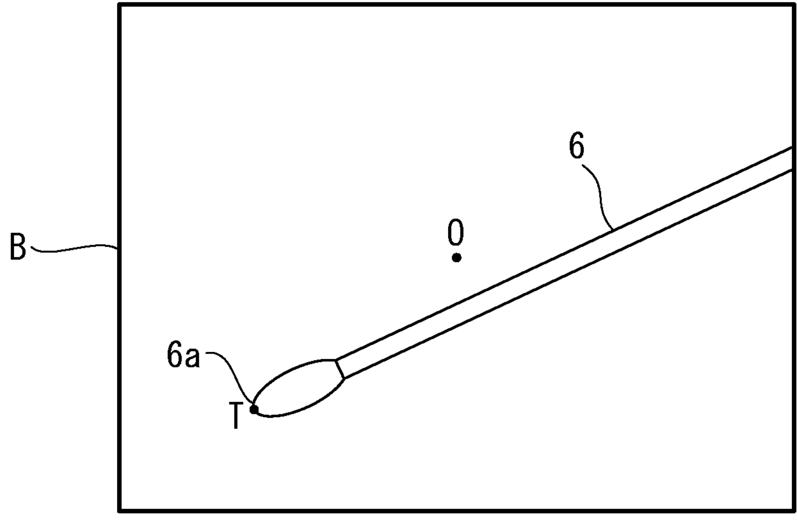
FIG. 18B illustrates an endoscope image indicating the position of a target point in the position and orientation of FIG. 18A.
Figure 19A:
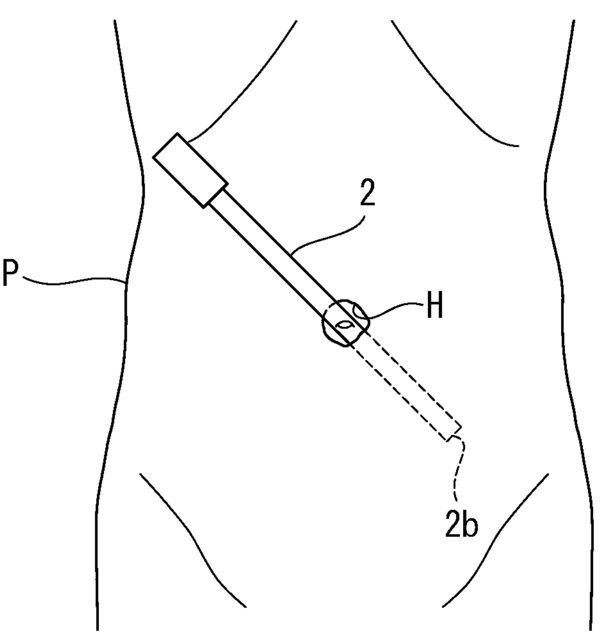
FIG. 19A illustrates another example of the position and orientation of the endoscope.

As illustrated in FIGS. 18A and 19A, the endoscope 2 is inserted into an abdominal cavity through a hole H formed on a body wall, and the position and orientation of the endoscope 2 are changed with a supporting point disposed at the position of the hole H. The position and orientation of the endoscope 2 are a position and an orientation on a coordinate system fixed to a subject P with respect to the supporting point.

Figure 19B:
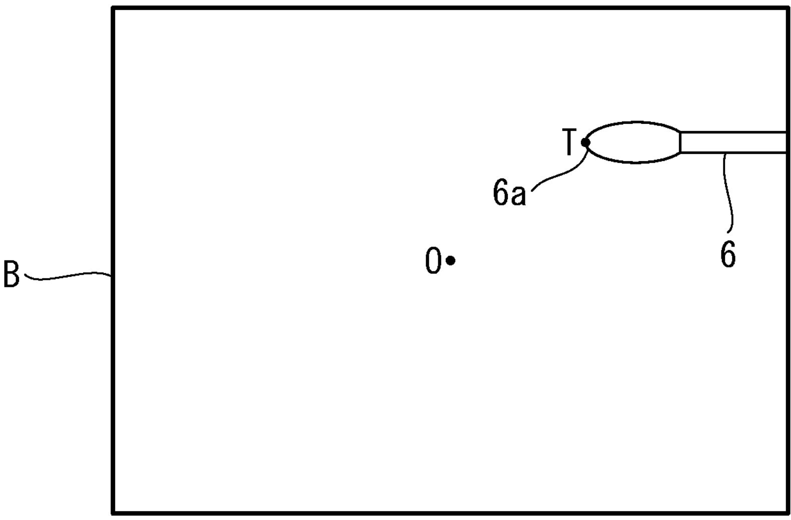
FIG. 19B illustrates an endoscope image indicating the position of the target point in the position and orientation of FIG. 19A.

In modifications illustrated in FIGS. 18A to 19B, a plurality of offset parameters for the positions and orientations of the endoscope 2 are set in advance or are set by an operator, e.g., a surgeon during a surgical operation. The offset parameter determination unit 13 determines an offset parameter corresponding to the position and orientation of the endoscope 2. Thus, as illustrated in FIGS. 18B and 19B, the target point T is set at a position corresponding to the position and orientation of the endoscope 2.

With this configuration, scene information can be acquired without the need for an input operation by the operator.

In the foregoing embodiments, the target point T is offset with respect to the fiducial point O in the three-dimensional direction. Alternatively, the target point T may be offset with respect to the fiducial point O in the two-dimensional direction or the one-dimensional direction.

For example, in one modification, the scene information acquisition unit 12 may detect the two-dimensional moving vector V along the YZ plane orthogonal to the optical axis A, and the offset parameter determination unit 13 may determine a two-dimensional offset parameter for the target point T to be offset in a direction parallel to the YZ plane with respect to the fiducial point O. In another modification, the scene information acquisition unit 12 may detect the one-dimensional moving vector V in the Z direction parallel to the optical axis A, and the offset parameter determination unit 13 may determine a one-dimensional offset parameter for the target point T to be offset only in the X direction with respect to the fiducial point O.

In the foregoing embodiments, the fiducial point O is a point on the optical axis A of the field of view F. The fiducial point may be set at any position in the field of view F, for example, outside the optical axis A.

In the foregoing embodiments, the target point T is a point in the field of view F. Alternatively, the target point T may be set in a two-dimensional or three-dimensional region. In this case, the controller 1 may cause the endoscope 2 to start following the surgical instrument 6 when the tip 6*a* of the surgical instrument 6 moves out of the region of the target point T.

Figure 20A:
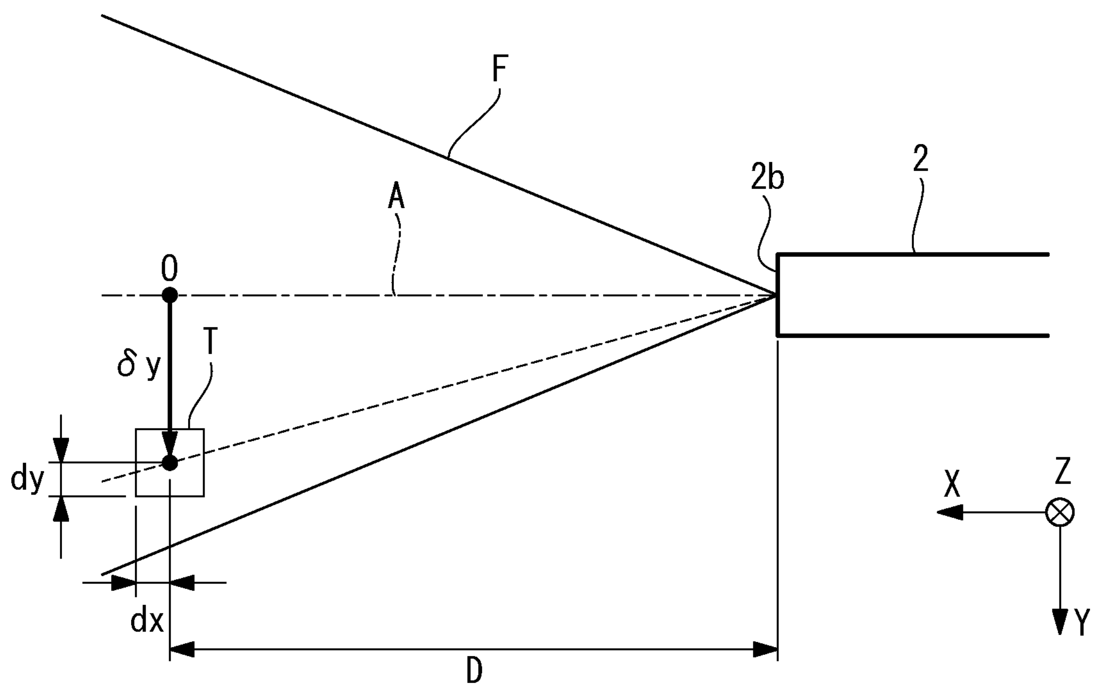
FIG. 20A is an explanatory drawing of a two-dimensional or three-dimensional target point set in the field of view of the endoscope.
Figure 20B:
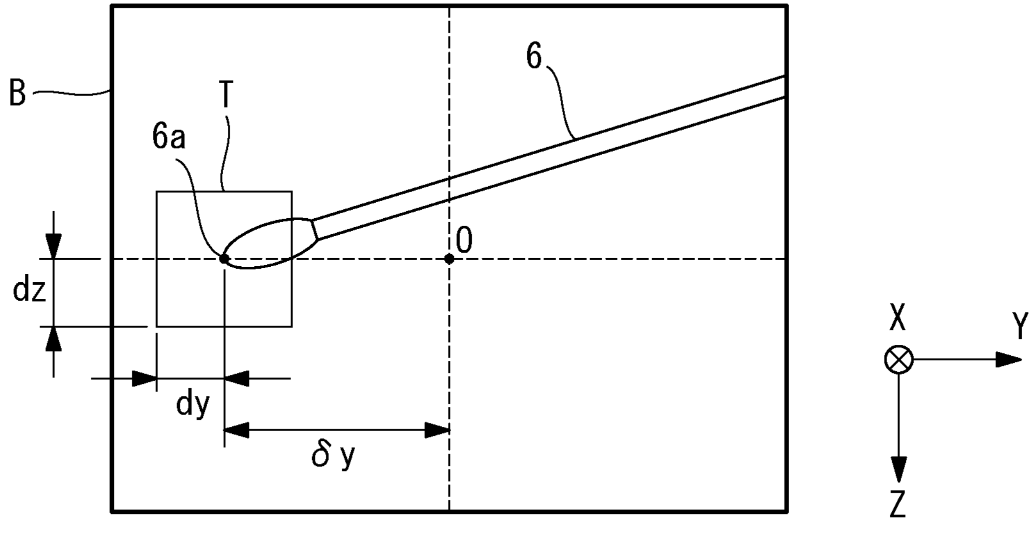
FIG. 20B is an explanatory drawing of a two-dimensional or three-dimensional target point in an endoscope image.

For example, as illustrated in FIGS. 20A and 20B, the target point T is a region of a rectangular solid having predetermined dimensions dx, dy, and dz in the X, Y, and Z directions. In the first to fourth embodiments, a region around the three-dimensional position calculated from the moving vector V is set as the target point T. In the fifth embodiment, a region around the position inputted by the operator is set as the target point T.

In the foregoing embodiments, the position information acquisition unit 11 acquires position information from the endoscope image B. Alternatively, position information may be acquired by using another means.

In one modification, the position information acquisition unit 11 may acquire position information from a three-dimensional position measuring device disposed outside a body. For example, the three-dimensional position measuring device may measure the position of a first marker attached to the endoscope 2 and the position of a second marker attached to the surgical instrument 6 and calculate, from the two measured positions, the three-dimensional position of the tip 6*a* of the surgical instrument 6 with respect to the tip 2*b* of the endoscope 2.

In another modification, the position information acquisition unit 11 may acquire position information from a three-dimensional scanner mounted in the endoscope 2. The three-dimensional scanner may measure the three-dimensional positions of the surgical instrument 6 and a biological tissue in the field of view F of the endoscope 2 by scanning light or ultrasonic waves.

Figure 21A:
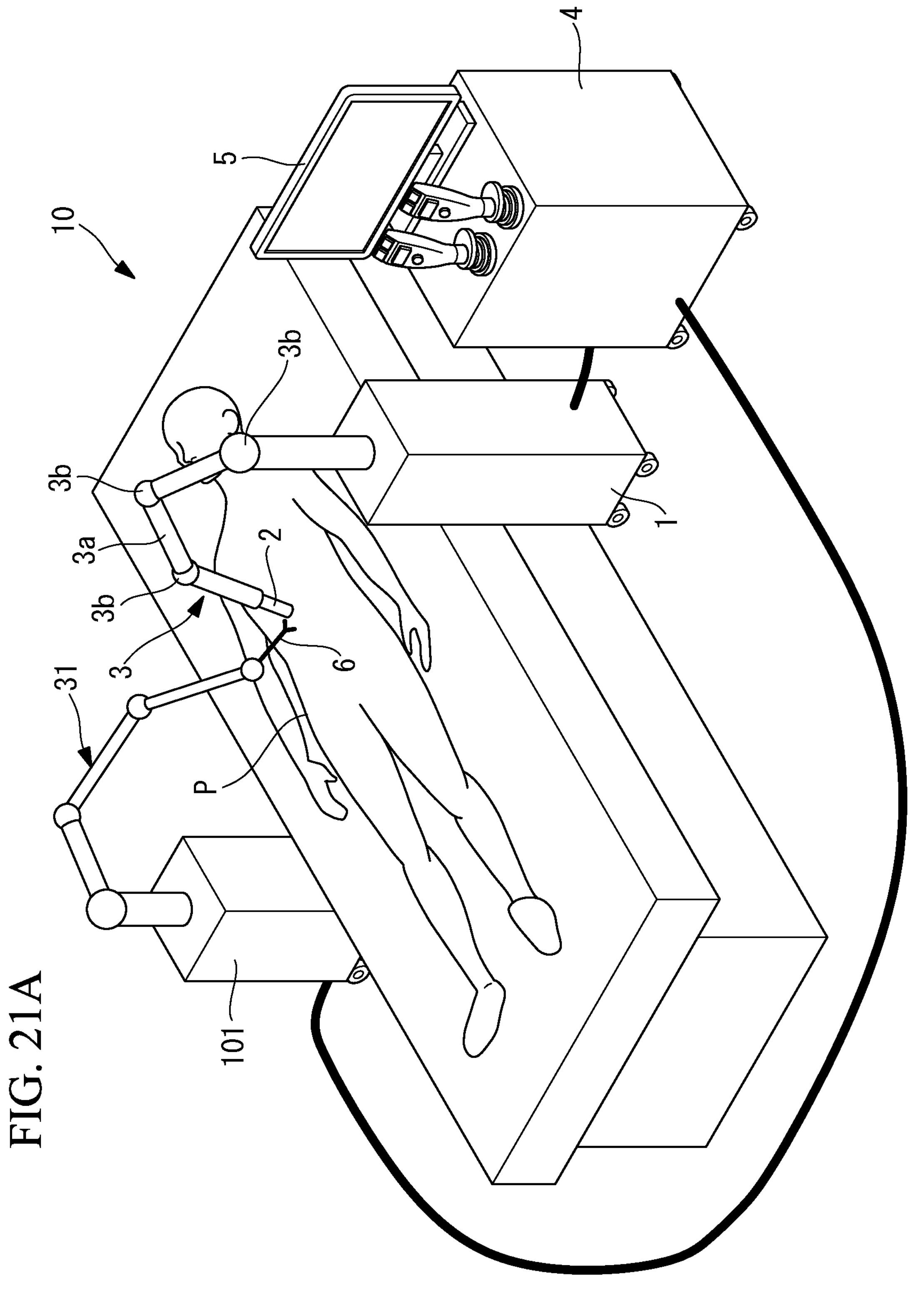
FIG. 21A illustrates an appearance of the overall configuration of a modification of the endoscope system in FIG. 1.
Figure 21B:
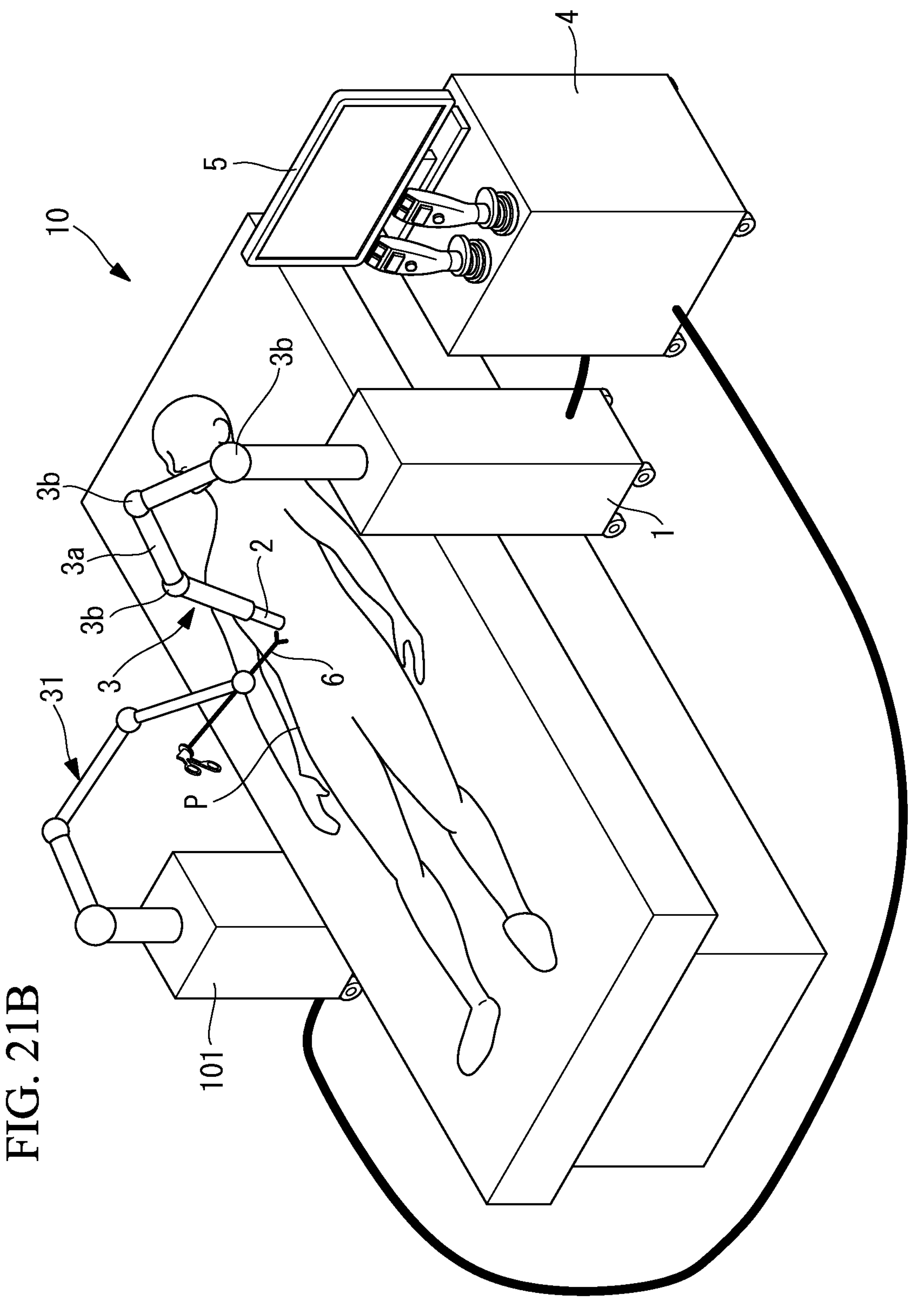
FIG. 21B illustrates an appearance of the overall configuration of another modification of the endoscope system in FIG. 1.

In another modification, as illustrated in FIGS. 21A and 21B, the position information acquisition unit 11 may acquire information on the positions of the endoscope 2 and the surgical instrument 6 from a first moving device 3 for moving the endoscope 2 and a second moving device 31 for moving the surgical instrument 6. Like the first moving device 3, the second moving device 31 holds the surgical instrument 6 with a robot arm or an electric holder and three-dimensionally changes the position and orientation of the surgical instrument 6 under the control of a controller 101. As illustrated in FIG. 21A, the surgical instrument 6 may be connected to the tip of the robot arm and may be integrated with the robot arm. As illustrated in FIG. 21B, the surgical instrument 6 may be a separate part held by a robot arm.

In the foregoing embodiments, the position information acquisition unit 11 acquires position information including the three-dimensional position of the surgical instrument 6. Alternatively, the position information acquisition unit 11 may acquire position information including the two-dimensional position of the surgical instrument 6.

For example, the surgical instrument 6, the target point T, and the fiducial point O may be disposed at two-dimensional positions on an image plane (YZ plane) of the endoscope image B, and the control unit 14 may set the target point T to be two-dimensionally offset with respect to the fiducial point O in the Y direction and the Z direction and cause the endoscope 2 to two-dimensionally follow the surgical instrument 6 in the Y direction and the Z direction.

REFERENCE SIGNS LIST

1 Controller
2 Endoscope
3 Moving device
6 Surgical instrument
6*a* Tip
10 Endoscope system
A Optical axis
B Endoscope image
F Field of view
L Ablating ling (anatomy information)
T Target point Fiducial point
P Patient, subject
V Moving vector (scene information)

The invention claimed is:

1. A controller comprising:

a processor comprising hardware, the processor being configured to:

acquire position information including a position of a surgical instrument, acquire scene information related to a procedure of a surgical operation, the scene information being information associated with a procedure scene to be observed through an endoscope, determine an offset parameter of a target point on a basis of the scene information, the offset parameter being a parameter that determines a position of the target point with respect to a predetermined fiducial point in a field of view of the endoscope, set the position of the target point with respect to the fiducial point on a basis of the offset parameter, and control a movement of the endoscope on a basis of the position of the target point and the position of the surgical instrument to three-dimensionally change a positional relationship between a tip of the surgical instrument and the endoscope such that the surgical instrument is disposed at the target point.

2. The controller according to claim 1, wherein the processor is configured to:

acquire a moving vector of the surgical instrument as the scene information; and determine the offset parameter on a basis of the moving vector.

3. The controller according to claim 2, wherein the processor is configured to determine the offset parameter that causes a region ahead of the surgical instrument in a moving direction of the surgical instrument to lie at a center of the field of view, on a basis of a direction of the moving vector.

4. The controller according to claim 1, wherein the processor is configured to estimate the procedure scene on the basis of the scene information and determines the offset parameter on a basis of the estimated procedure scene.

5. The controller according to claim 4, wherein the processor is configured to acquire a type of the surgical instrument as the scene information and estimates the procedure scene on a basis of the type of the surgical instrument.

6. The controller according to claim 5, wherein when the procedure scene is estimated to be an ablating scene, the processor is configured to determine the offset parameter that causes a region to be ablated by the surgical instrument to lie at a center of the field of view.

7. The controller according to claim 5, wherein when the procedure scene is estimated to be an unfolding scene, the processor is configured to set the offset parameter that causes a region to be unfolded by the surgical instrument to lie at a center of the field of view.

8. The controller according to claim 4, wherein the processor is configured to:

acquire an operating state of the surgical instrument as the scene information; and estimate the procedure scene on a basis of the operating state of the surgical instrument.

9. The controller according to claim 4, wherein the processor is configured to:

acquire anatomy information on a biological tissue in the field of view as the scene information; and estimate the procedure scene on a basis of the anatomy information.

10. The controller according to claim 1, wherein the processor is configured to acquire the position information including a three-dimensional position of the surgical instrument.

11. An endoscope system comprising:

an endoscope;

a moving device that moves the endoscope in a subject; and the controller according to claim 1.

12. The endoscope system according to claim 11, wherein the endoscope captures an image in the subject and acquires the image in the subject.

13. The endoscope system according to claim 11, wherein the moving device includes a robot arm that is connected to the endoscope and controls a position and orientation of the endoscope.

14. The endoscope system according to claim 13, wherein the processor is configured to:

calculate the position and orientation of the endoscope such that the target point is disposed at a tip of the surgical instrument, and control the robot arm on a basis of the calculated position and orientation of the endoscope.

* * * * *